(12) United States Patent
Penning et al.

(10) Patent No.: US 8,697,736 B2
(45) Date of Patent: *Apr. 15, 2014

(54) 1H-BENZIMIDAZOLE-4-CARBOXAMIDES SUBSTITUTED WITH PHENYL AT THE 2-POSITION ARE POTENT PARP INHIBITORS

(75) Inventors: Thomas D. Penning, Elmhurst, IL (US); Sheela A. Thomas, Libertyville, IL (US); Gui-Dong Zhu, Gurnee, IL (US); Virajkumar B. Gandhi, Gurnee, IL (US); Jianchun Gong, Deerfield, IL (US); Vincent L. Giranda, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 1565 days.

This patent is subject to a terminal disclaimer.

(21) Appl. No.: 11/536,994

(22) Filed: Sep. 29, 2006

(65) Prior Publication Data

US 2007/0179136 A1    Aug. 2, 2007

Related U.S. Application Data

(60) Provisional application No. 60/721,683, filed on Sep. 29, 2005.

(51) Int. Cl.
*A61K 31/4184* (2006.01)
*C07D 403/10* (2006.01)

(52) U.S. Cl.
USPC ........ 514/394; 514/218; 514/393; 548/309.4; 548/310.7

(58) Field of Classification Search
USPC ............. 514/218, 393, 394; 548/309.4, 310.7
See application file for complete search history.

(56) References Cited

U.S. PATENT DOCUMENTS

| 6,448,271 | B1 | 9/2002 | Lubisch et al. |
| 6,509,365 | B1 | 1/2003 | Lubisch et al. |
| 6,737,421 | B1 | 5/2004 | Lubish et al. |
| 7,122,679 | B2 * | 10/2006 | Ator et al. ..................... 548/418 |
| 2006/0229289 | A1 | 10/2006 | Zhu et al. |
| 2007/0072912 | A1 * | 3/2007 | Hideg et al. .................. 514/338 |
| 2009/0186877 | A1 * | 7/2009 | Giranda et al. ............... 514/218 |

FOREIGN PATENT DOCUMENTS

| CA | 2349227 | 5/2000 |
| EP | 1391457 | 2/2004 |
| WO | 00/29384 | 5/2000 |
| WO | 00/32579 | 6/2000 |
| WO | 2004/096793 | 11/2004 |

OTHER PUBLICATIONS

King "Med. chem. principle and practive" p. 206-208 (1994).*
White, A.W. et al., Potentiation of cytotoxic drug activity in human tumour cell lines, by amine-substituted 2-arylbenzimidazole-4-carboxamide PARP-1 inhibitor, Bioorganic & Medicinal Chemistry Letters, 2004, 2433-2437, vol. 14.
PCT/US2006/038169 Search Report.

* cited by examiner

*Primary Examiner* — Celia Chang
(74) *Attorney, Agent, or Firm* — Lisa V. Mueller; Michael Best & Friedrich LLP

(57) ABSTRACT

Compound having formula (I)

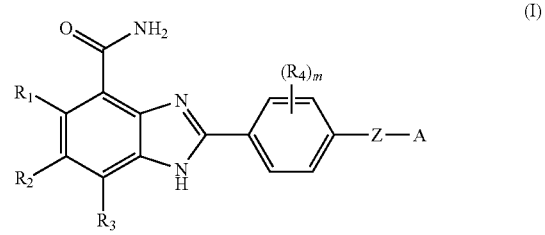

inhibit the PARP enzyme and are useful for treating a disease or a disorder associated with PARP. Also disclosed are pharmaceutical compositions comprising compounds having formula (I), methods of treatment comprising compounds having formula (I), and methods of inhibiting the PARP enzyme comprising compounds having formula (I).

8 Claims, No Drawings

1H-BENZIMIDAZOLE-4-CARBOXAMIDES SUBSTITUTED WITH PHENYL AT THE 2-POSITION ARE POTENT PARP INHIBITORS

This application claims priority to U.S. Provisional Application Ser. No. 60/721,683, filed Sep. 29, 2005.

FIELD OF THE INVENTION

This invention relates to 1H-benzimidazole-4-carboxamides, their preparation, and their use as inhibitors of the enzyme poly(ADP-ribose)polymerase for the preparation of drugs.

BACKGROUND OF THE INVENTION

Poly(ADP-ribose)polymerase (PARP) or poly(ADP-ribose)synthase (PARS) has an essential role in facilitating DNA repair, controlling RNA transcription, mediating cell death, and regulating immune response. These actions make PARP inhibitors targets for a broad spectrum of disorders. PARP inhibitors have demonstrated efficacy in numerous models of disease, particularly in models of ischemia reperfusion injury, inflammatory disease, degenerative diseases, protection from adverse effects of cytoxic compounds, and the potentiation of cytotoxic cancer therapy. PARP has also been indicated in retroviral infection and thus inhibitors may have use in antiretroviral therapy. PARP inhibitors have been efficacious in preventing ischemia reperfusion injury in models of myocardial infarction, stroke, other neural trauma, organ transplantation, as well as reperfusion of the eye, kidney, gut and skeletal muscle. Inhibitors have been efficacious in inflammatory diseases such as arthritis, gout, inflammatory bowel disease, CNS inflammation such as MS and allergic encephalitis, sepsis, septic shock, hemmorhagic shock, pulmonary fibrosis, and uveitis. PARP inhibitors have also shown benefit in several models of degenerative disease including diabetes (as well as complications) and Parkinsons disease. PARP inhibitors can ameliorate the liver toxicity following acetaminophen overdose, cardiac and kidney toxicities from doxorubicin and platinum based antineoplastic agents, as well as skin damage secondary to sulfur mustards. In various cancer models, PARP inhibitors have been shown to potentiate radiation and chemotherapy by increasing cell death of cancer cells, limiting tumor growth, decreasing metastasis, and prolonging the survival of tumor-bearing animals.

SUMMARY OF THE INVENTION

In one embodiment, this invention comprises compounds having formula (I)

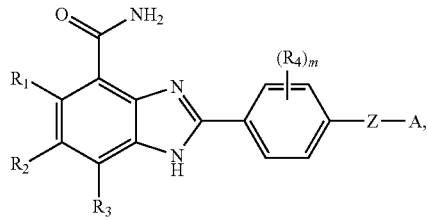

or a salt thereof, wherein $R_1$, $R_2$, and $R_3$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_AR_B$, and $(NR_AR_B)$carbonyl;

each $R_4$ is independently selected from the group consisting of hydrogen, halogen, alkyl, and haloalkyl;

m is 4;

Z is a bond or alkylenyl;

A is a nonaromatic 5 or 6-membered ring that contains 1 or 2 nitrogen atoms and, optionally, one sulfur or oxygen atom, wherein A is attached to Z through a carbon atom, and wherein the nonaromatic ring is optionally substituted with 1, 2, or 3 substituents selected from the group consisting of alkenyl, alkoxy, alkoxyalkyl, alkoxycarbonyl, alkoxycarbonylalkyl, alkyl, alkylcarbonyl, alkylcarbonylalkyl, alkynyl, aryl, arylalkyl, carboxy, cycloalkyl, cycloalkylalkyl, cyano, haloalkoxy, haloalkyl, halogen, heteroaryl, heteroarylalkyl, heterocycle, heterocyclealkyl, heterocyclecarbonyl, heterocyclesulfonyl, hydroxy, hydroxyalkyl, $NR_CR_D$, $(NR_CR_D)$alkyl, $(NR_CR_D)$carbonyl, $(NR_CR_D)$carbonylalkyl, $(NR_CR_D)$sulfonyl, and oxo; and $R_A$, $R_B$, $R_C$, and $R_D$ are independently selected from the group consisting of hydrogen, alkyl, cycloalkyl, and alkycarbonyl.

DETAILED DESCRIPTION OF THE INVENTION

In another embodiment, this invention comprises compounds having formula (I)

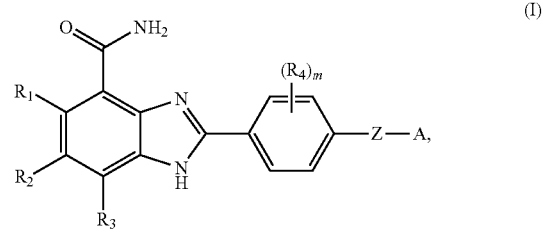

or a salt thereof, wherein $R_1$, $R_2$, and $R_3$ are independently selected from the group consisting of hydrogen and halogen;

each $R_4$ is independently selected from the group consisting of hydrogen, halogen, and haloalkyl;

m is 4;

Z is a bond or alkylenyl;

A is a nonaromatic 5 or 6-membered ring that contains 1 nitrogen atom, wherein A is attached to Z through a carbon atom, and wherein the nonaromatic ring is optionally substituted with 1, 2, or 3 substituents selected from the group consisting of alkoxycarbonyl, alkyl, arylalkyl, cycloalkyl, cycloalkylalkyl, and heterocyclealkyl.

In another embodiment, this invention comprises a pharmaceutical composition comprising a compound having formula (I), wherein Z is a bond.

In another embodiment, this invention comprises a pharmaceutical composition comprising a compound having formula (I), wherein Z is alkylenyl.

In another embodiment, this invention comprises a pharmaceutical composition comprising a compound having formula (I), wherein A is selected from the group consisting of

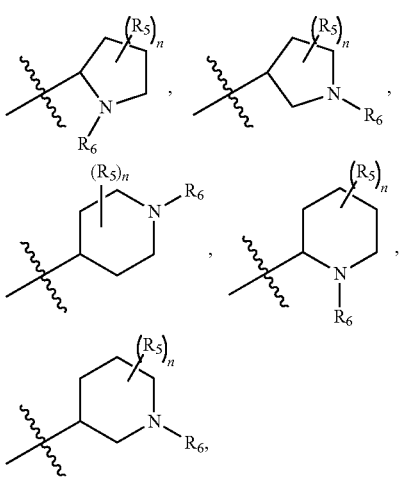

each R$_5$ is independently selected from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, heterocycle, heterocyclealkyl, heteroaryl, heteroarylalkyl, hydroxy, hydroxyalkyl, NR$_D$, (NR$_C$R$_D$)alkyl, (NR$_C$R$_D$)carbonyl, (NR$_C$R$_D$)carbonylalkyl, and (NR$_C$R$_D$)sulfonyl;

R$_6$ is selected from the group consisting of hydrogen, alkenyl, alkoxyalkyl, alkoxycarbonyl, alkoxycarbonylalkyl, alkyl, alkynyl, aryl, arylalkyl, cycloalkyl, cycloalkylalkyl, heterocycle, heterocyclealkyl, heteroaryl, heteroarylalkyl, hydroxyalkyl, (NR$_C$R$_D$)alkyl, (NR$_C$R$_D$)carbonyl, (NR$_C$R$_D$) carbonylalkyl, and (NR$_C$R$_D$)sulfonyl;

R$_C$ and R$_D$ are independently selected from the group consisting of hydrogen and alkyl;

and n is 0, 1, 2, or 3.

In another embodiment, this invention comprises a pharmaceutical composition comprising a compound having formula (I), wherein Z is a bond;

A is selected from the group consisting of

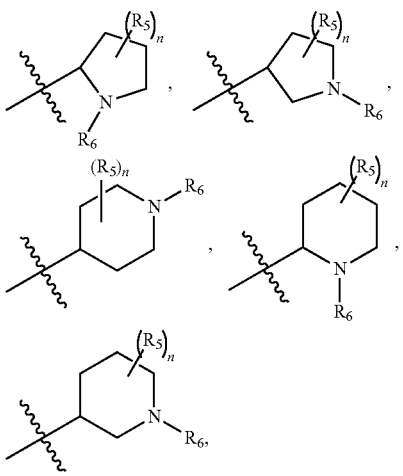

each R$_5$ is independently selected from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, heterocycle, heterocyclealkyl, heteroaryl, heteroarylalkyl, hydroxy, hydroxyalkyl, NR$_D$, (NR$_C$R$_D$)alkyl, (NR$_C$R$_D$)carbonyl, (NR$_C$R$_D$)carbonylalkyl, and (NR$_C$R$_D$)sulfonyl;

R$_6$ is selected from the group consisting of hydrogen, alkenyl, alkoxyalkyl, alkoxycarbonyl, alkoxycarbonylalkyl, alkyl, alkynyl, aryl, arylalkyl, cycloalkyl, cycloalkylalkyl, heterocycle, heterocyclealkyl, heteroaryl, heteroarylalkyl, hydroxyalkyl, (NR$_C$R$_D$)alkyl, (NR$_C$R$_D$)carbonyl, (NR$_C$R$_D$) carbonylalkyl, and (NR$_C$R$_D$)sulfonyl;

R$_C$ and R$_D$ are independently selected from the group consisting of hydrogen and alkyl;

and n is 0, 1, 2, or 3.

In another embodiment, this invention comprises a pharmaceutical composition comprising a compound having formula (I), wherein A is selected from the group consisting of

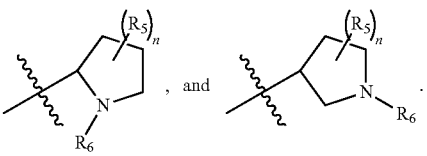

In another embodiment, this invention comprises a pharmaceutical composition comprising a compound having formula (I), wherein A is selected from the group consisting of

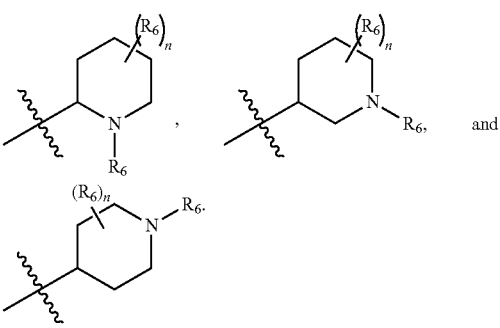

In another embodiment, this invention comprises a pharmaceutical composition comprising a compound having formula (I), wherein R$_1$, R$_2$, and R$_3$ are hydrogen.

In another embodiment, this invention comprises a pharmaceutical composition comprising a compound having formula (I), wherein R$_2$ is halogen.

In another embodiment, this invention comprises a pharmaceutical composition comprising a compound having formula (I), wherein each R$_4$ is hydrogen.

In another embodiment, this invention comprises a pharmaceutical composition comprising a compound having formula (I), or a salt thereof, and therapeutically acceptable carrier.

In another embodiment, this invention comprises a method of inhibiting PARP in a mammal comprising administering thereto a therapeutically acceptable amount of a compound having formula (I) or a salt thereof.

In another embodiment, this invention comprises a method of treating cancer in a mammal comprising administering thereto a therapeutically acceptable amount of a compound having formula (I) or a salt thereof.

In another embodiment, this invention comprises a method for decreasing tumor volume in a mammal comprising administering thereto a therapeutically acceptable amount of a compound having formula (I) or a salt thereof.

In another embodiment, this invention comprises a method of treating leukemia, colon cancer, glioblastomas, lymphomas, melanomas, carcinomas of the breast, or cervical carcinomas in a mammal comprising administering thereto a therapeutically acceptable amount of a compound having formula (I) or a salt thereof.

In another embodiment, this invention comprises a method of potentiation of cytotoxic cancer therapy in a mammal comprising administering thereto a therapeutically acceptable amount of a compound having formula (I) or a salt thereof.

In another embodiment, this invention comprises a method of potentiation of radiation therapy in a mammal comprising administering thereto a therapeutically acceptable amount of a compound having formula (I) or a salt thereof.

In another embodiment, this invention comprises a method of treating ischemia reperfusion injury associated with, but not limited to, myocardial infarction, stroke, other neural trauma, and organ transplantation, in a mammal comprising administering thereto a therapeutically acceptable amount of a compound having formula (I) or a salt thereof.

In another embodiment, this invention comprises a method of reperfusion including, but not limited to, reperfusion of the eye, kidney, gut and skeletal muscle, in a mammal comprising administering thereto a therapeutically acceptable amount of a compound having formula (I) or a salt thereof.

In another embodiment, this invention comprises a method of treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal comprising administering thereto a therapeutically acceptable amount of a compound having formula (I) or a salt thereof.

In another embodiment, this invention comprises a method of treating immunological diseases or disorders such as rheumatoid arthritis and septic shock in a mammal comprising administering thereto a therapeutically acceptable amount of a compound having formula (I) or a salt thereof.

In another embodiment, this invention comprises a method of treating degenerative disease including, but not limited to, diabetes and Parkinsons disease, in a mammal comprising administering thereto a therapeutically acceptable amount of a compound having formula (I) or a salt thereof.

In another embodiment, this invention comprises a method of treating hypoglycemia in a mammal comprising administering thereto a therapeutically acceptable amount of a compound having formula (I) or a salt thereof.

In another embodiment, this invention comprises a method of treating retroviral infection in a mammal comprising administering thereto a therapeutically acceptable amount of a compound having formula (I) or a salt thereof.

In another embodiment, this invention comprises a method of treating liver toxicity following acetominophen overdose in a mammal comprising administering thereto a therapeutically acceptable amount of a compound having formula (I) or a salt thereof.

In another embodiment, this invention comprises a method of treating cardiac and kidney toxicities from doxorubicin and platinum based antineoplastic agents in a mammal comprising administering thereto a therapeutically acceptable amount of a compound having formula (I) or a salt thereof.

In another embodiment, this invention comprises a method of treating skin damage secondary to sulfur mustards in a mammal comprising administering thereto a therapeutically acceptable amount of a compound having formula (I) or a salt thereof.

In another embodiment, this invention comprises a use of a compound having formula (I), or a salt thereof, to prepare a medicament for inhibiting the PARP enzyme in a mammal in recognized need of such treatment.

In another embodiment, this invention comprises a use of a compound having formula (I), or a salt thereof, to prepare a medicament for inhibiting tumor growth in a mammal in recognized need of such treatment.

In another embodiment, this invention comprises a use of a compound having formula (I), or a salt thereof, to prepare a medicament for treating cancer in a mammal in recognized need of such treatment.

In another embodiment, this invention comprises a use of a compound having formula (I), or a salt thereof, to prepare a medicament for treating leukemia, colon cancer, glioblastomas, lymphomas, melanomas, carcinomas of the breast, or cervical carcinomas in a mammal in a mammal in recognized need of such treatment.

In another embodiment, this invention comprises a use of a compound having formula (I), or a salt thereof, to prepare a medicament for potentiation of cytotoxic cancer therapy in a mammal comprising administering thereto a therapeutically acceptable amount of a compound having formula (I) or a salt thereof.

In another embodiment, this invention comprises a use of a compound having formula (I), or a salt thereof, to prepare a medicament for potentiation of radiation in a mammal comprising administering thereto a therapeutically acceptable amount of a compound having formula (I) or a salt thereof.

In another embodiment, this invention comprises a use of a compound having formula (I), or a salt thereof, to prepare a medicament for treating ischemia reperfusion injury associated with, but not limited to, myocardial infarction, stroke, other neural trauma, and organ transplantation, in a mammal comprising administering thereto a therapeutically acceptable amount of a compound having formula (I) or a salt thereof.

In another embodiment, this invention comprises a use of a compound having formula (I), or a salt thereof, to prepare a medicament for treating reperfusion including, but not limited to, reperfusion of the eye, kidney, gut and skeletal muscle, in a mammal comprising administering thereto a therapeutically acceptable amount of a compound having formula (I) or a salt thereof.

In another embodiment, this invention comprises a use of a compound having formula (I), or a salt thereof, to prepare a medicament for treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal comprising administering thereto a therapeutically acceptable amount of a compound having formula (I) or a salt thereof.

In another embodiment, this invention comprises a use of a compound having formula (I), or a salt thereof, to prepare a medicament for treating immunological diseases or disorders such as rheumatoid arthritis and septic shock in a mammal comprising administering thereto a therapeutically acceptable amount of a compound having formula (I) or a salt thereof.

In another embodiment, this invention comprises a use of a compound having formula (I), or a salt thereof, to prepare a medicament for treating degenerative disease including, but not limited to, diabetes and Parkinsons disease, in a mammal comprising administering thereto a therapeutically acceptable amount of a compound having formula (I) or a salt thereof.

In another embodiment, this invention comprises a use of a compound having formula (I), or a salt thereof, to prepare a medicament for treating hypoglycemia in a mammal comprising administering thereto a therapeutically acceptable amount of a compound having formula (I) or a salt thereof.

In another embodiment, this invention comprises a use of a compound having formula (I), or a salt thereof, to prepare a medicament for treating retroviral infection in a mammal comprising administering thereto a therapeutically acceptable amount of a compound having formula (I) or a salt thereof.

In another embodiment, this invention comprises a use of a compound having formula (I), or a salt thereof, to prepare a medicament for treating liver toxicity following acetominophen overdose in a mammal comprising administering thereto a therapeutically acceptable amount of a compound having formula (I) or a salt thereof.

In another embodiment, this invention comprises a use of a compound having formula (I), or a salt thereof, to prepare a medicament for treating cardiac and kidney toxicities from doxorubicin and platinum based antineoplastic agents in a mammal comprising administering thereto a therapeutically acceptable amount of a compound having formula (I) or a salt thereof.

In another embodiment, this invention comprises a use of a compound having formula (I), or a salt thereof, to prepare a medicament for treating skin damage secondary to sulfur mustards in a mammal comprising administering thereto a therapeutically acceptable amount of a compound having formula (I) or a salt thereof.

As used throughout this specification, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, attached to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means at least one alkoxy group, as defined herein, attached to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, attached to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, attached to the parent molecular moiety through an alkyl group, as defined herein.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, attached to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, attached to the parent molecular moiety through an oxygen atom. Representative examples of alkylcarbonyloxy include, but are not limited to, acetyloxy, ethylcarbonyloxy, and tert-butylcarbonyloxy.

The term "alkylenyl" as used herein, means a divalent group derived from a straight or branched chain hydrocarbon of from 1 to 6 carbon atoms. Representative examples include, but are not limited to, —$CH_2$—, —$CH(CH_3)$—, —$C(CH_3)_2$—, —$CH_2CH_2$—, —$CH_2CH_2CH_2CH_2CH_2$—, —$CH_2CH_2CH_2$—, —$CH_2CH(CH_3)CH_2$—, The term "alkylthio" as used herein, means an alkyl group, as defined herein, attached to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, attached to the parent molecular moiety through an alkyl group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl group or a naphthyl group.

The aryl groups of this invention can be optionally substituted with one, two, three, four, or five substituents independently selected from the group consisting of alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, heterocycle, hydroxy, hydroxyalkyl, mercapto, nitro, —$NR_ER_F$, and ($NR_E R_F$)carbonyl.

The term "arylalkyl" as used herein, means an aryl group, as defined herein, attached to the parent molecular moiety through an alkyl group, as defined herein. Representative examples of arylalkyl include, but are not limited to, benzyl, 2-phenylethyl, 3-phenylpropyl, 1-methyl-3-phenylpropyl, and 2-naphth-2-ylethyl.

The term "carbonyl" as used herein, means a —C(O)— group.

The term "carboxy" as used herein, means a —$CO_2H$ group.

The term "cyano" as used herein, means a —CN group.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The cycloalkyl groups of this invention are optionally substituted with 1, 2, 3, or 4 substituents selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, oxo, —NR$_E$R$_F$, and (NR$_E$R$_F$)carbonyl.

The term "cycloalkylalkyl" as used herein, means a cycloalkyl group, as defined herein, attached to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "formyl" as used herein, means a —C(O)H group.

The term "halo" or "halogen" as used herein, means —Cl, —Br, —I or —F.

The term "haloalkoxy" as used herein, means at least one halogen, as defined herein, attached to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, attached to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a phenyl group or the 5 or 6 membered heteroaryl ring is fused to another 5 or 6 membered heteroaryl ring. Nitrogen heteroatoms contained within the heteroaryl may be optionally oxidized to the N-oxide. The heteroaryl is connected to the parent molecular moiety through any carbon atom contained within the heteroaryl while maintaining proper valence. Representative examples of heteroaryl include, but are not limited to, benzothienyl, benzoxadiazolyl, cinnolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, tetrazolyl, thiadiazolyl, thiazolyl, thienopyridinyl, thienyl, triazolyl, and triazinyl.

The heteroaryl groups of this invention are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —NR$_E$R$_F$, and (NR$_E$R$_F$)carbonyl.

The term "heteroarylalkyl" as used herein, means a heteroaryl, as defined herein, attached to the parent molecular moiety through an alkyl group, as defined herein. Representative examples of heteroarylalkyl include, but are not limited to, pyridinymethyl.

The term "heterocycle" or "heterocyclic" as used herein, means a monocyclic or bicyclic heterocyclic ring. The monocyclic heterocyclic ring consists of a 3, 4, 5, 6, 7, or 8 membered ring containing at least one heteroatom independently selected from O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocyclic ring consists of a monocyclic heterocyclic ring fused to a cycloalkyl group or the monocyclic heterocyclic ring fused to a phenyl group or the monocyclic heterocyclic ring fused to another monocyclic heterocyclic ring. The heterocycle is connected to the parent molecular moiety through any carbon or nitrogen atom contained within the heterocycle while maintaining proper valence. Representative examples of heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The heterocycles of this invention are substituted with 0, 1, 2, or 3 substituents independently selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —NR$_E$R$_F$, (NR$_E$R$_F$)carbonyl, and phenylalkoxycarbonyl.

The term "heterocyclealkyl" as used herein, means a heterocycle, as defined herein, attached to the parent molecular moiety through an alkyl group, as defined herein.

The term "heterocyclecarbonyl" as used herein, means a heterocycle, as defined herein, attached to the parent molecular moiety through a carbonyl group, as defined herein.

The term "heterocyclesulfonyl" as used herein, means a heterocycle, as defined herein, attached to the parent molecular moiety through a sulfonyl group.

The term "hydroxy" as used herein, means an —OH group.

The term "hydroxyalkyl" as used herein, means at least one hydroxy group, as defined herein, is attached to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "nonaromatic" as used herein, means that a 4 membered nonaromatic ring contains zero double bonds, a 5 membered nonaromatic ring contains zero or one double bond, a 6, 7, or 8 membered nonaromatic ring contains zero, one, or two double bonds.

The term "NR$_A$R$_B$" as used herein, means two groups, R$_A$ and R$_B$, which are attached to the parent molecular moiety through a nitrogen atom. R$_A$ and R$_B$ are each independently hydrogen, alkyl, alkylcarbonyl, and cycloalkyl. Representative examples of NR$_A$R$_B$ include, but are not limited to, amino, methylamino, acetylamino, and acetylmethylamino.

The term "(NR$_A$R$_B$)carbonyl" as used herein, means a NR$_A$R$_B$ group, as defined herein, attached to the parent molecular moiety through a carbonyl group, as defined herein. Representative examples of (NR$_A$R$_B$)carbonyl include, but are not limited to, aminocarbonyl, (methylamino)carbonyl, (dimethylamino)carbonyl, and (ethylmethylamino)carbonyl.

The term "NR$_C$R$_D$" as used herein, means two groups, R$_C$ and R$_D$, which are attached to the parent molecular moiety through a nitrogen atom. R$_C$ and R$_D$ are each independently hydrogen, alkyl, alkylcarbonyl, and cycloalkyl. Representative examples of NR$_C$R$_D$ include, but are not limited to, amino, methylamino, acetylamino, and acetylmethylamino.

The term "(NR$_C$R$_D$)carbonyl" as used herein, means a NR$_C$R$_D$ group, as defined herein, attached to the parent molecular moiety through a carbonyl group, as defined herein. Representative examples of (NR$_C$R$_D$)carbonyl include, but are not limited to, aminocarbonyl, (methylamino)carbonyl, (dimethylamino)carbonyl, and (ethylmethylamino)carbonyl.

The term "(NR$_C$R$_D$)carbonylalkyl" as used herein, means a (NR$_C$R$_D$)carbonyl group, as defined herein, attached to the parent molecular moiety through an alkyl group, as defined herein.

The term "(NR$_C$R$_D$)sulfonyl" as used herein, means a NR$_D$ group, as defined herein, attached to the parent molecular moiety through a sulfonyl group, as defined herein. Representative examples of (NR$_D$)sulfonyl include, but are not limited to, aminosulfonyl, (methylamino)sulfonyl, (dimethylamino)sulfonyl, and (ethylmethylamino)sulfonyl.

The term "NR$_E$R$_F$" as used herein, means two groups, R$_E$ and R$_F$, which are attached to the parent molecular moiety through a nitrogen atom. R$_E$ and R$_F$ are each independently hydrogen, alkyl, alkylcarbonyl, and cycloalkyl. Representative examples of NR$_E$R$_F$ include, but are not limited to, amino, methylamino, acetylamino, and acetylmethylamino.

The term "(NR$_E$R$_F$)carbonyl" as used herein, means a NR$_E$R$_F$ group, as defined herein, attached to the parent molecular moiety through a carbonyl group, as defined herein. Representative examples of (NR$_E$R$_F$)carbonyl include, but are not limited to, aminocarbonyl, (methylamino)carbonyl, (dimethylamino)carbonyl, and (ethylmethylamino)carbonyl.

The term "oxo" as used herein, means a =moiety.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl.

Compounds of this invention can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. This invention contemplates various stereoisomers and mixtures thereof and are specifically included within the scope of this invention. Stereoisomers include enantiomers, diastereomers, and mixtures of enantiomers or diastereomers. Individual stereoisomers of compounds of this invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Compounds of this invention were named by ACD/ChemSketch version 5.06 (developed by Advanced Chemistry Development, Inc., Toronto, ON, Canada) or were given names which appeared to be consistent with ACD nomenclature.

Inhibition of PARP

Notinamide[2,5',8-3H]adenine dinucleotide and strepavidin SPA beads were purchased from Amersham Biosciences (UK) Recombinant Human Poly(ADP-Ribose) Polymerase (PARP) purified from *E. coli* and 6-Biotin-17-NAD$^+$, were purchase from Trevigen, Gaithersburg, Md. NAD$^+$, Histone, aminobenzamide, 3-amino benzamide and Calf Thymus DNA (dcDNA) were purchased from Sigma, St. Louis, Mo. Stem loop oligonucleotide containing MCAT sequence was obtained from Qiagen. The oligos were dissolved to 1 mM in annealing buffer containing 10 mM Tris HCl pH 7.5, 1 mM EDTA, and 50 mM NaCl, incubated for 5 min at 95° C., and followed by annealing at 45° C. for 45 minutes. Histone H1 (95% electrophoretically pure) was purchased from Roche, Indianapolis, Ind. Biotinylated histone H1 was prepared by treating the protein with Sulfo-NHS-LC-Biotin from Pierce Rockford, Ill. The biotinylation reaction was conducted by slowly and intermittently adding 3 equivalents of 10 mM Sulfo-NHS-LC-Biotin to 100 μM Histone H1 in phosphate-buffered saline, pH 7.5, at 4° C. with gentle vortexing over 1 min followed by subsequent 4° C. incubation for 1 hr. Streptavidin coated (FlashPlate Plus) microplates were purchased from Perkin Elmer, Boston, Mass.

PARP1 assay was conducted in PARP assay buffer containing 50 mM Tris pH 8.0, 1 mM DTT, 4 mM MgCl$_2$. PARP reactions contained 1.5 μM [$^3$H]-NAD$^+$ (1.6 uCi/mmol), 200 nM biotinylated histone H1, 200 nM slDNA, and 1 nM PARP enzyme. Auto reactions utilizing SPA bead-based detection were carried out in 100 μl volumes in white 96 well plates. Reactions were initiated by adding 50 μl of 2× NAD$^+$ substrate mixture to 50 μl of 2× enzyme mixture containing PARP and DNA. These reactions were terminated by the addition of 150 μl of 1.5 mM benzamide (~1000-fold over its IC50). 170 μl of the stopped reaction mixtures were transferred to streptavidin Flash Plates, incubated for 1 hour, and counted using a TopCount microplate scintillation counter. The K$_i$ data (nM) were determined from inhibition curves at various substrate concentrations and are shown in Table 1.

TABLE 1

Inhibition of PARP

| | | | | | | | |
|---|---|---|---|---|---|---|---|
| 1.9 | 12.6 | 23.7 | 2.3 | 13.1 | 14.5 | 11.6 | 3.3 |
| 37 | 5.5 | 11.7 | 2.7 | 2.8 | 2.7 | 15.5 | 15.6 |
| 4.5 | 10.5 | 14.6 | 3.9 | 8.4 | 7.2 | 7.8 | 10.4 |
| 6.1 | 9.9 | 7.7 | 4.2 | 8.7 | 7.5 | 31.6 | 5 |
| 9.2 | 2.2 | 7.4 | 5.6 | 12.2 | 7.9 | 6.6 | 9.9 |
| 10.8 | 66 | 9.4 | 41 | 5.1 | 6.1 | 3 | 7.8 |
| 3 | 65 | 3.8 | 68 | 1.6 | 2.6 | 20.5 | 3.7 |
| 13 | 19.9 | 12.8 | 57 | 19.2 | 10.6 | 16.8 | 10.6 |
| 5.3 | 2.8 | 11.4 | 6.4 | 5.3 | 31.5 | 8.7 | 8.9 |
| 7.2 | 12.5 | 7.2 | 7 | 1.6 | 1.6 | 9.4 | 5.2 |
| 11.4 | 20.1 | 10.4 | 3.2 | 2.8 | 2.1 | 6.1 | 2.3 |
| 2.8 | 3 | 2 | | | | | |

Cellular PARP Assay:

C41 cells were treated with a compound of this invention for 30 minutes in 96 well plate. PARP was then activated by damaging DNA with 1 mM H$_2$O$_2$ for 10 minutes. The cells were then washed with ice-cold PBS once and fixed with pre-chilled methanol:acetone (7:3) at −20° C. for 10 minutes. After air-drying, the plates were rehydrated with PBS and blocked 5% non-fat dry milk in PBS-tween (0.05%) (blocking solution) for 30 minutes at room temperature. The cells were incubated with anti-PAR antibody 10H (1:50) in Blocking solution at 37° C. for 60 minutes followed by washing with PBS-Tween20 5 times, and incubation with goat anti-mouse fluorescein 5(6)-isothiocyanate-coupled antibody (1:50) and 1 μg/ml 4',6-diamidino-2-phenylindole (DAPI) in blocking solution at 37° C. for 60 minutes. After washing with PBS-Tween20 5 times, the analysis was performed using an fmax Fluorescence Microplate Reader (Molecular Devices, Sunnyvalle, Calif.), set at the excitation wavelength of 490 nm and emission wavelength of 528 nm fluorescein 5(6)-isothiocyanate (FITC) or the excitation wavelength of 355 nm and emission wavelength of 460 nm (DAPI). The PARP activity (FITC signal) was normalized with cell numbers (DAPI).

The cellular assay measures the formation of poly ADP-ribose by PARP within cells and demonstrates that compounds of this invention penetrate cell membranes and inhibit PARP in intact cells. The $EC_{50}$, for representative compounds of this invention are provided in Table 2.

TABLE 2

Cellular Activity $EC_{50}$ (nM)

| | | | | | | | |
|---|---|---|---|---|---|---|---|
| 18 | 35 | 3 | 7.5 | 1.3 | 5.2 | 39 | 39 |
| 3.2 | 239 | 21 | 8.3 | 8 | 20 | 8.6 | 26 |
| 5.1 | 174 | 7.1 | 5.6 | 5.9 | >1000 | 86 | 42 |
| 1.9 | 4.1 | 7 | 39 | 3.3 | 4.4 | 10.7 | 12 |
| 4.3 | 36 | 8.4 | 1.9 | 3.3 | 32 | 15 | 88 |
| 7.7 | 37 | 19 | 108 | 40 | 6.7 | 14 | 5.2 |
| 22 | 11 | 4.2 | 139 | 2.3 | 8.3 | 5.7 | 52 |
| 26 | 57 | 15.8 | 45 | 5 | 5.1 | 12.4 | 2.1 |
| 5.2 | 27 | 12.6 | 1.7 | 5.7 | 37 | 3.6 | 8.4 |
| 6.8 | 6.7 | 10.1 | 18.5 | 5.4 | 2.3 | 3.5 | 0.4 |
| 2 | 1.2 | 7 | 1.3 | 13 | 1.1 | 0.3 | |

As PARP inhibitors, the compounds of this invention have numerous therapeutic applications related to, ischemia reperfusion injury, inflammatory diseases, degenerative diseases, protection from adverse effects of cytotoxic compounds, and potentiation of cytotoxic cancer therapy. In particular, compounds of this invention potentiate radiation and chemotherapy by increasing cell death of cancer cells, limiting tumor growth, decreasing metastasis, and prolonging the survival of tumor-bearing mammals. Compounds of Formula (I) can treat leukemia, colon cancer, glioblastomas, lymphomas, melanomas, carcinomas of the breast, and cervical carcinomas.

Other therapeutic applications include, but are not limited to, retroviral infection, arthritis, gout, inflammatory bowel disease, CNS inflammation, multiple sclerosis, allergic encephalitis, sepsis, septic shock, hemmorhagic shock, pulmonary fibrosis, uveitis, diabetes, Parkinsons disease, myocardial infarction, stroke, other neural trauma, organ transplantation, reperfusion of the eye, reperfusion of the kidney, reperfusion of the gut, reperfusion of skeletal muscle, liver toxicity following acetominophen overdose, cardiac and kidney toxicities from doxorubicin and platinum based antineoplastic agents, and skin damage secondary to sulfur mustards. (G. Chen et al. Cancer Chemo. Pharmacol. 22 (1988), 303; C. Thiemermann et al., Proc. Natl. Acad. Sci. USA 94 (1997), 679-683 D. Weltin et al. Int. J. Immunopharmacol. 17 (1995), 265-271; H. Kröger et al. Inflammation 20 (1996), 203-215; W. Ehrlich et al. Rheumatol. Int. 15 (1995), 171-172; C. Szabo et al., Proc. Natl. Acad. Sci. USA 95 (1998), 3867-3872; S. Cuzzocrea et al. Eur. J. Pharmacol. 342 (1998), 67-76; V. Burkhart et al., Nature Medicine (1999), 5314-19).

Determination of In Vivo Efficacy

PARP Inhibitors in Combination with Cisplatin in an Early Staged MX-1 Breast Carcinoma Xenograft Model 0.2 cc of 1:10 MX-1 tumor brei, was injected subcutaneously into the flank of female SCID mice (Charles River Labs) on study day 0. On day 15, tumors were size matched (188±25 mm$^3$) and the animals were placed into one of two therapy groups:

Group 1 vehicle (s.c. OMP×7)+Cisplatin 6 mg/kg/day (i.p., qd×1)

Group 2 PARPi 25 mg/kg/day (s.c. OMP×7)+Cisplatin 6 mg/kg/day (i.p., qd×1) The vehicle for both the PARP inhibitor and cisplatin was 0.9% NaCl. There were 8-10 rats in each group. Treatment with the PARPi began on day 16 while cisplatin treatment was started on day 18. At various intervals following tumor cell inoculation, the individual tumor dimensions were serially measured using calibrated microcalipers and the tumor volumes calculated according to the formula $V=L\times W^2/2$ (V:volume, L:length, W:width). Mice were humanely euthanized when the tumor volumes reached a predetermined size.

Table 3 shows the average tumor volume for both treatment groups. The PARP inhibitor, potentiated cisplatin activity as reflected by the enhanced antitumor activity at Day 48.

TABLE 3

| Compound | Dose (mg/kg/day) | Tumor Volume[a] (Day 48) |
|---|---|---|
| Vhl (PARPi)/Cis | 0/6 | 1389 ± 300 |
| PARPi/Cis | 25/6 | 519 ± 104 |

When used in the above or other treatments, a therapeutically effective amount of one of the compounds of this invention can be employed as a zwitterion or as a pharmaceutically acceptable salt. By a "therapeutically effective amount" of the compound of the invention is meant a sufficient amount of the compound to treat or prevent a disease or disorder ameliorated by a PARP inhibitor at a reasonable benefit/risk ratio applicable to any medical treatment. It will be understood, however, that the total daily usage of the compounds and compositions of this invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved.

By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. The salts can be prepared in situ during the final isolation and purification of the compounds of this invention or separately by reacting the free base of a compound of this invention with a suitable acid. Representative acids include, but are not limited to acetic, citric, aspartic, benzoic, benzenesulfonic, butyric, fumaric, hydrochloric, hydrobromic, hydroiodic, lactic, maleic, methanesulfonic, pamoic, pectinic, pivalic, propionic, succinic, tartaric, phosphic, glutamic, and p-toluenesulfonic. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained.

A compound of this invention may be administered as a pharmaceutical composition containing a compound of this invention in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions can be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or non-aqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions can also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Compounds of this invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of this invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Total daily dose of the compositions of the invention to be administered to a human or other mammal host in single or divided doses may be in amounts, for example, from 0.0001 to 300 mg/kg body weight daily and more usually 1 to 300 mg/kg body weight. The dose, from 0.0001 to 300 mg/kg body, may be given twice a day.

Abbreviations which have been used in the descriptions of the examples that follow are: DBU for 1,8-diazabicyclo[5.4.0]undec-7-ene; DMF for N,N-dimethylformamide; DMSO for dimethylsulfoxide; $Et_2O$ for diethyl ether; EtOAc for ethyl acetate; EtOH for ethanol; HPLC for high pressure liquid chromatography; LDA for lithium diisopropylamide; MeOH for methanol; psi for pounds per square inch; TFA for trifluoroacetic acid; THF for tetrahydrofuran, and TMS for trimethylsilane.

Compounds having formula I may be made by synthetic chemical processes, examples of which are shown herein below. It is meant to be understood that the order of the steps in the processes may be varied, that reagents, solvents and reaction conditions may be substituted for those specifically mentioned, and that vulnerable moieties may be protected and deprotected, as necessary.

Scheme 1

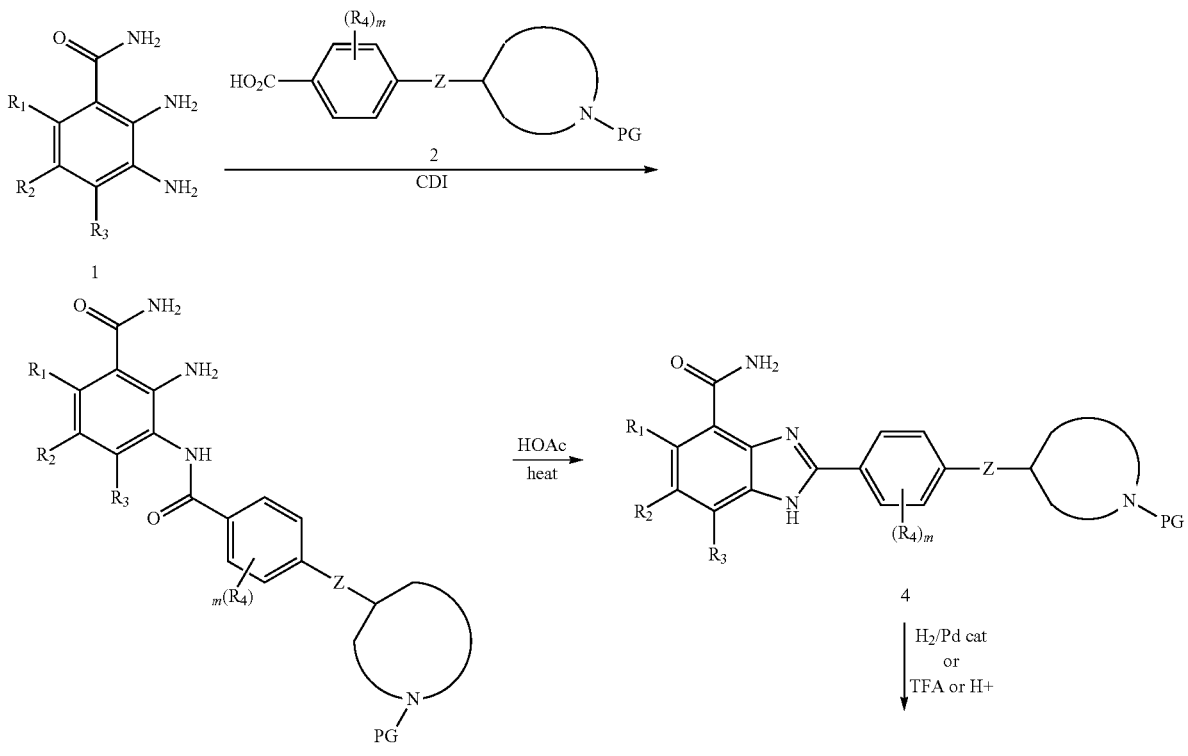

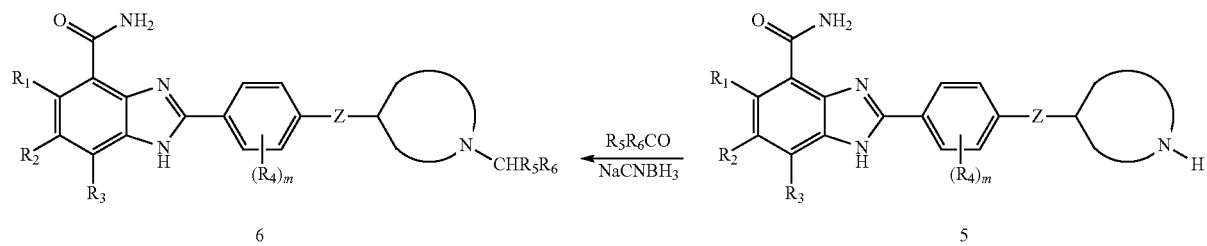

As shown in Scheme 1, compounds having formula 1 may be converted to compounds having formula 3 by reacting the former, compounds having formula 2 wherein PG symbolizes a protecting group, and an amide forming reagent, such as 1,1'-carbonyldiimidazole (CDI). Compounds having formula 3 may be converted to compounds having formula 4 when treated with an acid, such as acetic acid, and heat. The protecting group of compounds having formula 4 may be removed using hydrogenolysis conditions (for CBZ) or acidic conditions (for BOC) to give compounds having formula 5. Compounds having formula 5 may be alkylated under reductive amination conditions with either a ketone or aldehyde to yield compounds having formula 6.

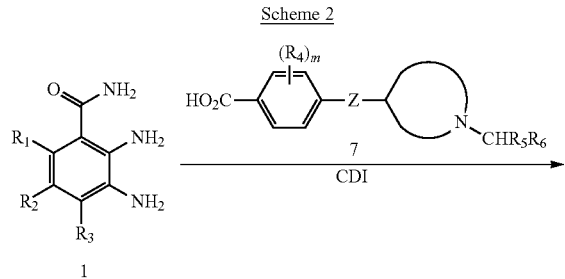

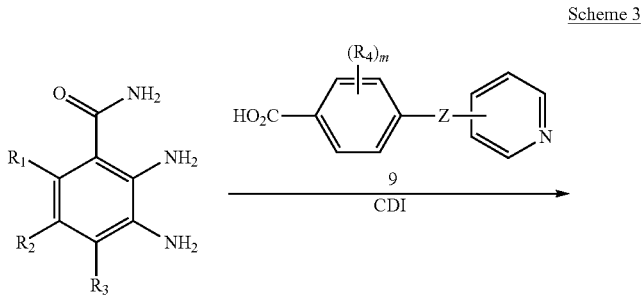

As shown in Scheme 2, compounds having formula 1 may be converted to compounds having formula 8 by reacting the former with compounds having formula 7, and an amide forming reagent, such as 1,1'-carbonyldiimidazole (CDI). Compounds having formula 8 may be converted to compounds having formula 6 when treated with an acid, such as acetic acid, and heat.

-continued

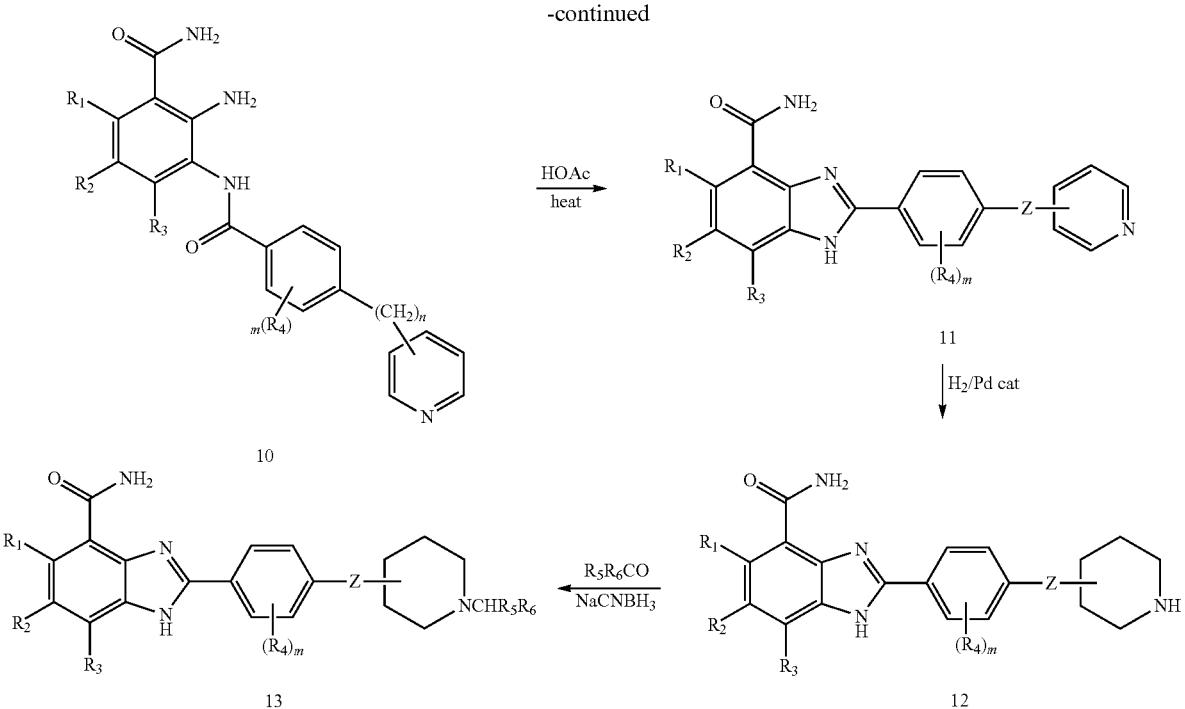

As shown in Scheme 3, compounds having formula 1 may be converted to compounds having formula 10 by reacting the former, compounds having formula 9, and an amide forming reagent, such as 1,1'-carbonyldiimidazole (CDI). Compounds having formula 10 may be converted to compounds having formula 11 when treated with an acid, such as acetic acid, and heat. Compounds having formula 11 may be reduced with hydrogen and a catalyst such as palladium to form compounds having formula 12. Compounds having formula 12 may be alkylated under reductive amination conditions using either a ketone or aldehyde to yield compounds having formula 13.

Scheme 4

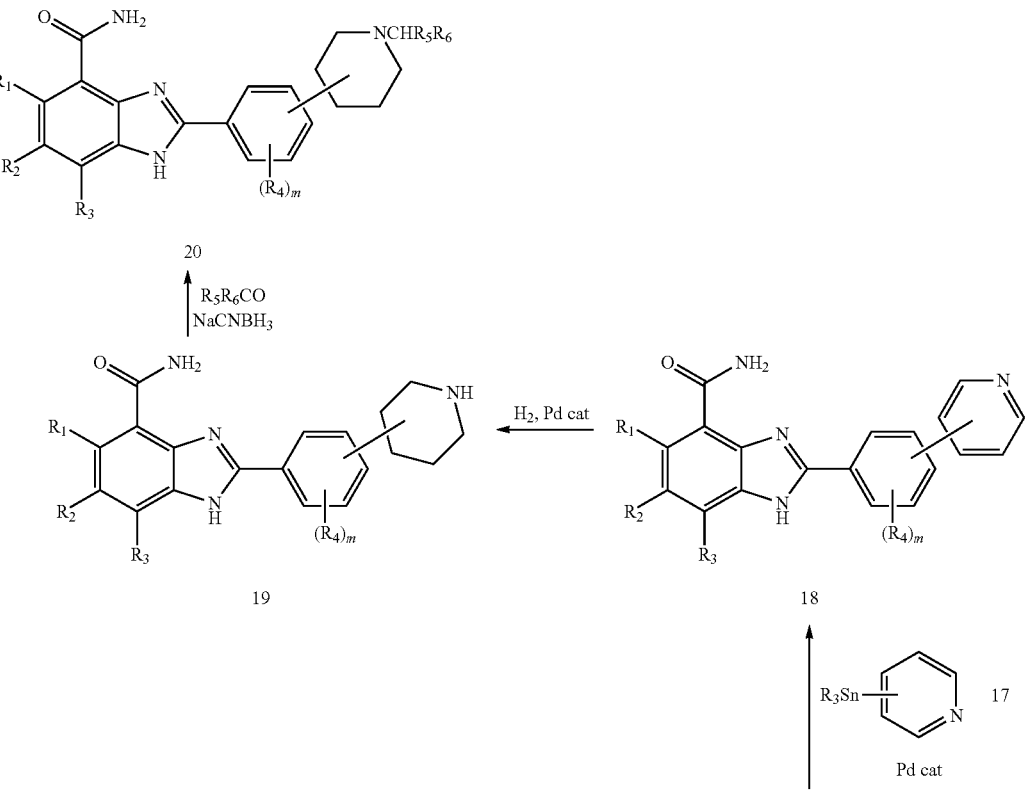

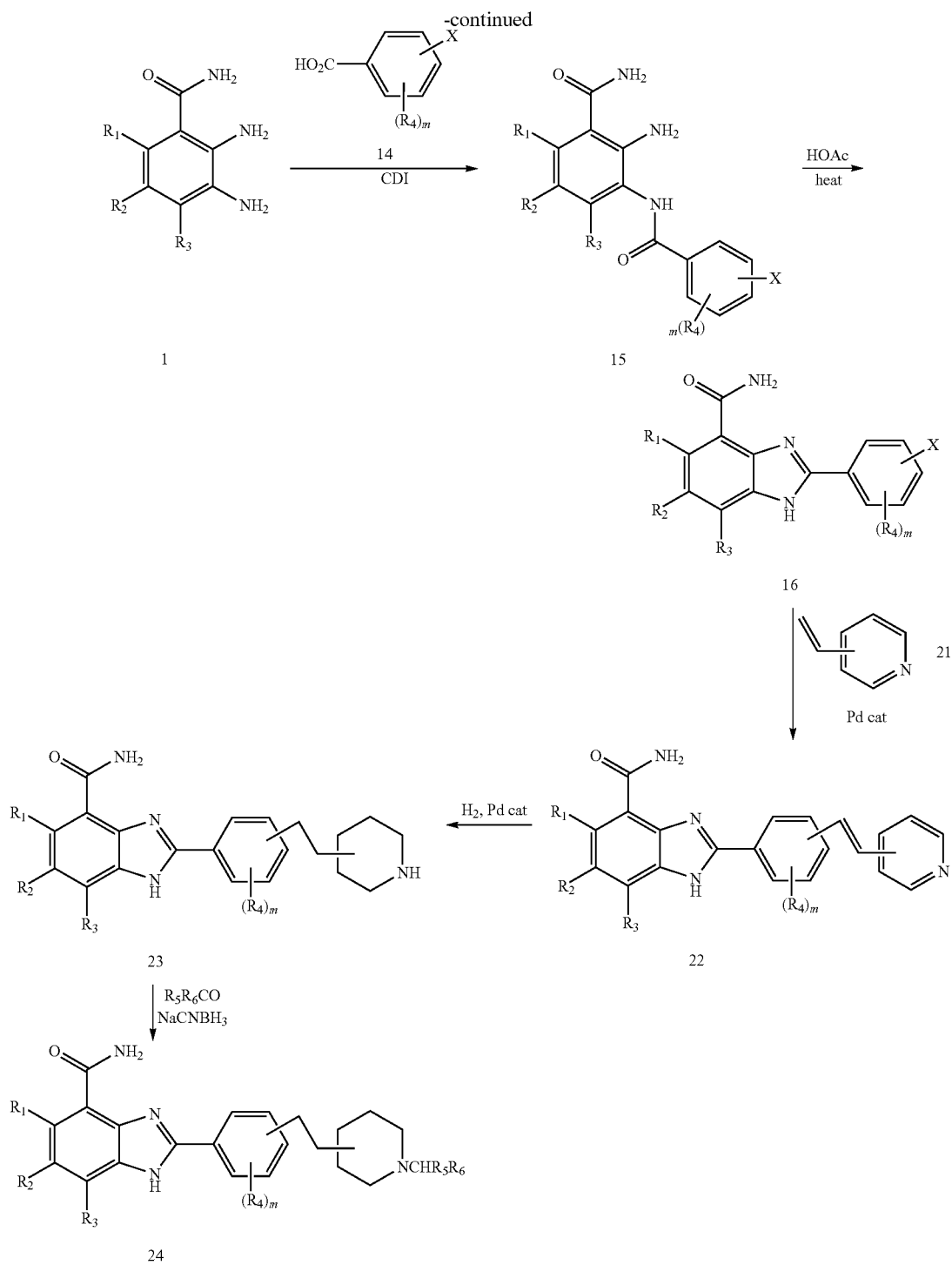

As shown in Scheme 4, compounds having formula 1 may be converted to compounds having formula 15 by reacting the former, compounds having formula 14 wherein X is halogen, and an amide forming reagent, such as 1,1'-carbonyldiimidazole (CDI). Compounds having formula 15 may be converted to compounds having formula 16 when treated with an acid, such as acetic acid, and heat. Compounds having formula 16 may be converted to compounds having formula 22 by reacting the former and compounds having formula 21 under standard palladium-catalyzed conditions. Compounds having formula 22 may be reduced with hydrogen and a catalyst such as palladium to yield compounds having formula 23 which may be alkylated under reductive amination conditions using either a ketone or aldehyde to provide compounds having formula 24.

Additionally compounds having formula 16 may be converted to compounds having formula 18 by treating the former with compounds having formula 17 under standard palladium-catalyzed conditions. Compounds having formula 18 may be reduced to provide compounds having formula 19 which may be alkylated under reductive amination conditions using either a ketone or aldehyde to provide compounds having formula 20.

The following Examples are intended as an illustration of and not a limitation upon the scope of the invention as defined in the attached claims. The compounds of this invention can be prepared by a variety of synthetic routes.

Example 1

2-(4-piperidin-4-ylphenyl)-1H-benzimidazole-4-carboxamide

Example 1A tert-butyl 4-(4-(2-amino-3-carbamoylphenylcarbamoyl)phenyl)piperidine-1-carboxylate A solution of tert-butyl 4-(4-carboxyphenyl)-piperidine-1-carboxylate (1 g) in pyridine (3 mL) and DMF (3 mL) at 40° C. was stirred for 30 minutes, treated with carbonyl diimidazole (CDI, 0.55 g), stirred for 1 hour, treated with 2,3-diaminobenzamide dihydrochloride (synthesized as described in U.S. Pat. No. 6,737,421, 0.73 g), stirred for 1 hour at ambient temperature, treated with isopropanol, (10 mL), cooled for 18 hours at 0° C. and filtered. The filtrant was dissolved in water (10 mL), treated with 50% aqueous NaOH (0.26 mL), stirred for 3 hours at ambient temperature and filtered.

Example 1B 2-(4-piperidin-4-ylphenyl)-1H-benzimidazole-4-carboxamide

A solution of EXAMPLE 1A (0.175 g) in acetic acid (2 mL) at reflux was stirred for 90 minutes and concentrated. The concentrate was dissolved in water, treated with 50% aqueous NaOH (0.2 mL) and filtered. The filtrate was concentrated and purified by high performance liquid chromatography (HPLC) on a C18 column with 0-100% $CH_3CN$/water/0.1% trifluoroacetic acid (TFA). $^1H$ NMR (DMSO-$d_6$) δ 9.25 (s, 1H), 8.61 (s, 1H), 8.34 (s, 1H), 8.22 (d, J=8.42 Hz, 1H), 7.87 (d, J=6.55 Hz, 1H), 7.74 (d, J=7.18 Hz, 2H), 7.46 (d, J=8.11 Hz, 2H), 7.35 (t, J=7.80 Hz, 1H), 3.42 (d, J=12.48 Hz, 2H), 3.01-3.09 (m, 2H), 2.97 (ddd, J=12.01, 8.58, 3.43 Hz, 1H), 2.00 (s, 2H), 1.84 (qd, J=13.05, 3.90 Hz, 2H).

Example 2

2-(4-piperidin-2-ylphenyl)-1H-benzimidazole-4-carboxamide

Example 2A 2-(4-piperidin-2-ylphenyl)-1H-benzimidazole-4-carboxamide

A mixture of 2,3-diaminobenzamide dihydrochloride (1 g), 4-pyridin-2-ylbenzaldehyde (0.82 g) and 10% Pd/C (0.3 g) in methanol (30 mL) at reflux was stirred for 18 hours, cooled, filtered through diatomaceous earth (Celite®) and concentrated. The concentrate was crystallized from methanol.

Example 2B 2-(4-piperidin-2-ylphenyl)-1H-benzimidazole-4-carboxamide

A mixture of EXAMPLE 2A (0.905 g) and $PtO_2$ in acetic acid (20 mL) at ambient temperature under hydrogen (60 psi) was stirred for 4.5 hours, filtered through a nylon membrane and concentrated. The concentrate was purified by chromatography on silica gel with 10% methanol/dichloromethane. 1H NMR (DMSO-$d_6$) δ 9.33 (s, 1H), 8.33 (d, J=8.11 Hz, 2H), 7.89 (d, J=7.49 Hz 1H), 7.73-7.81 (m, 4H), 7.36 (t, J=7.64 Hz, 1H), 4.27 (dd, J=11.70, 2.96 Hz, 1H), 3.17 (s, 1H), 3.03 (td, J=12.24, 4.21 Hz, 2H), 1.81-1.97 (m, 6H), 1.63-1.66 (m, 1H).

Example 3

2-(4-(1-methyl-piperidin-2-yl)phenyl)-1H-benzimidazole-4-carboxamide

A solution of EXAMPLE 2 (0.05 g) and 36% formaldehyde in water (0.012 mL) in methanol (1 mL) was treated with sodium cyanoborohydride (0.01 g) and acetic acid (0.2 mL), stirred for 18 hours and concentrated. The concentrate was purified by chromatography on silica gel with 10% methanol/dichloromethane. $^1H$ NMR (DMSO-$d_6$) δ 9.35 (s, 1H), 8.15-8.24 (m, 2H), 7.87 (d, J=7.49 Hz 1H), 7.72 (d, J=6.86 Hz, 2H), 7.53 (d, J=7.80 Hz, 2H), 7.32-7.39 (m, 1H), 2.99 (s, 1H), 2.82 (s, 1H), 1.91 (s, 5H), 1.79 (d, J=14.66 Hz, 2H), 1.67 (s, 3H), 1.31-1.48 (m, 1H).

Example 4

2-(4-(1-ethylpiperidin-2-yl)phenyl)-1H-benzimidazole-4-carboxamide

This compound was prepared by substituting acetaldehyde for formaldehyde in EXAMPLE 3. $^1H$ NMR (DMSO-$d_6$) δ 9.34 (s, 1H), 8.32 (s, 1H), 8.15 (s, 1H), 7.82-7.92 (m, 3H), 7.75 (d, J=7.93 Hz, 2H), 7.36 (t, J=7.63 Hz, 1H), 4.10 (q, J=5.19 Hz, 1H), 3.17 (d, J=5.19 Hz, 2H), 2.09 (s, 1H), 2.04 (s, 1H), 1.78-1.91 (s, 5H), 1.19 (s, 1H), 1.06-1.15 (m, 2H), 0.87-0.95 (m, 1H).

Example 5

2-(4-(1-isopropyl-piperidin-2-yl)phenyl)-1H-benzimidazole-4-carboxamide

This compound was prepared by substituting acetone for formaldehyde in EXAMPLE 3. $^1H$ NMR (DMSO-$d_6$) δ 9.35 (s, 1H), 8.17 (m, 2H), 7.86 (d, J=7.67 Hz 1H), 7.73 (s, 3H), 7.52 (s, 1H), 7.33 (m, 1H), 2.93 (s, 1H), 2.16 (s, 1H), 1.73 (s, 3H), 1.48 (s, 2H), 1.26 (d, J=6.14 Hz, 2H), 1.11 (m, 1H), 0.95 (s, 2H), 0.76 (s, 2H).

Example 6

2-(4-piperidin-3-ylphenyl)-1H-benzimidazole-4-carboxamide

Example 6A 2-(4-piperidin-3-ylphenyl)-1H-benzimidazole-4-carboxamide

This compound was prepared by substituting pyridin-3-ylbenzoic acid for tert-butyl 4-(4-carboxy-phenyl)-piperidine-1-carboxylate in EXAMPLE 1.

Example 6B

2-(4-piperidin-3-ylphenyl)-1H-b benzimidazole-4-carboxamide

This compound was prepared by substituting EXAMPLE 6A for EXAMPLE 2A in EXAMPLE 2. $^1$H NMR (DMSO-$d_6$) δ 9.33 (s, 1H), 8.16 (d, J=7.93 Hz, 1H), 7.85 (d, J=7.63 Hz 1H), 7.73 (d, J-8.24 Hz, 2H), 7.45 (d, J=8.24 Hz, 2H), 7.32 (t, J=7.78 Hz, 1H), 3.03 (d, J=11.29 Hz, 1H), 2.97 (d, J=12.21 Hz, 1H), 2.67-2.75 (m, 1H), 2.52-2.62 (m, 2H), 1.91 (s, 1H), 1.66-1.71 (m, 1H), 1.63 (dd, J=12.21, 3.05 Hz, 1H), 1.52 (d, J=12.21 Hz, 1H).

Example 7

2-(4-(1-isopropyl-piperidin-3-yl)phenyl)-1H-benzimidazole-4-carboxamide

This compound was prepared by substituting EXAMPLE 6 for EXAMPLE 2 in EXAMPLE 5. $^1$H NMR (DMSO-$d_6$) δ 9.32 (s, 1H), 8.21 (d, J=8.29 Hz, 2H), 7.87 (d, J=7.36 Hz 1H), 7.73 (d, J=7.67 Hz, 2H), 7.55 (d, J=8.29 Hz, 2H), 7.34 (t, J=7.83 Hz, 1H), 3.43 (m, 4H), 3.16 (d, J=5.22 Hz, 2H), 2.98 (m, 1H) 1.90-2.07 (m, 2H), 1.79-1.89 (m, 1H), 1.27 (d, J=4.60 Hz, 6H).

Example 8

2-(4-(1-methyl-piperidin-3-yl)phenyl)-1H-benzimidazole-4-carboxamide

This compound was prepared by substituting EXAMPLE 6 for EXAMPLE 2 in EXAMPLE 3. $^1$H NMR (DMSO-$d_6$) δ 9.32 (s, 1H), 8.15 (d, J=7.98 Hz, 2H), 7.85 (d, J=7.36 Hz 1H), 7.71 (d, J=7.06 Hz, 2H), 7.48 (t, J=7.83 Hz, 2H), 7.32 (t, J=7.83 Hz, 1H), 2.77-2.88 (m, 3H), 2.20 (s, 3H), 1.95-2.03 (m, 1H), 1.88-1.05 (m, 1H), 1.85 (s, 2H), 1.67-1.75 (m, 1H), 1.56-1.67 (m, 1H), 1.43 (dd, J=11.97, 3.99 Hz, 1H).

Example 9

2-(4-(1-ethyl-piperidin-3-yl)phenyl)-1H-benzimidazole-4-carboxamide

This compound was prepared by substituting EXAMPLE 6 for EXAMPLE 2 in EXAMPLE 4. $^1$H NMR (DMSO-$d_6$) δ 9.48 (s, 1H), 8.28 (d, J=8.29 Hz, 2H), 7.98 (d, J=7.36 Hz 1H), 7.84 (d, J=7.36 Hz, 2H), 7.60 (d, J=7.98 Hz, 2H), 7.45 (t, J=7.67 Hz, 1H), 3.00-3.08 (m, 2H), 2.92-2.98 (m, 1H), 2.50 (q, J=7.26 Hz, 2H), 2.13 (t, J=10.74 Hz, 1H), 2.04 (d, J=11.97 Hz, 1H), 1.97 (s, 2H), 1.82-1.90 (m, 1H), 1.67-1.78 (m, 1H), 1.61 (td, J=12.04, 3.53 Hz, 1H), 1.13 (t, J=7.21 Hz, 3H).

Example 10

2-(4-(1-benzyl-piperidin-3-yl)phenyl)-1H-benzimidazole-4-carboxamide

This compound was prepared by substituting benzaldehyde for formaldehyde in EXAMPLE 8. $^1$H NMR (DMSO-$d_6$) δ 9.34 (s, 1H), 8.13 (d, J=7.98 Hz, 2H), 7.93 (d, J=7.06 Hz 1H), 7.85 (d, J=7.36 Hz, 1H), 7.70 (d, J=7.36 Hz, 2H), 7.41-7.50 (m, 3H), 7.29-7.34 (m, 5H), 3.51 (s, 2H), 2.86 (m, 4H), 2.00-2.10 (m, 2H), 1.80 (s, 1H), 1.69-1.75 (m, 1H), 1.60-1.68 (m, 1H), 1.48-1.58 (m, 1H).

Example 11

2-(4-(1-phenethyl-piperidin-3-yl)phenyl)-1H-benzimidazole-4-carboxamide

This compound was prepared by substituting phenylacetaldehyde for formaldehyde in EXAMPLE 8. $^1$H NMR (DMSO-$d_6$) δ 9.35 (s, 1H), 8.14 (d, J=7.98 Hz, 2H), 7.85 (d, J=7.67 Hz 1H), 7.71 (d, J=7.06 Hz, 2H), 7.48 (d, J=8.29 Hz, 2H), 7.33 (t, J=7.67 Hz, 1H), 7.14-7.28 (m, 5H), 2.92-3.0 (m, 3H), 2.82-2.86 (m, 2H), 2.69-2.81 (m, 3H), 2.03-2.14 (m, 2H), 1.70-1.90 (m, 2H), 1.55-1.65 (m, 1H), 1.44-1.54 (m, 1H).

Example 12 benzyl 4-(3-(4-(4-carbamoyl-1H-benzimidazol-2-yl)phenyl)piperidin-1-ylmethyl)-1-carboxylate This compound was prepared by substituting benzyl 4-formylpiperidine-1-carboxylate for formaldehyde in EXAMPLE 8. $^1$H NMR (DMSO-$d_6$) δ 9.36 (s, 1H), 8.15 (d, J=7.98 Hz, 2H), 7.86 (d, J=7.36 Hz 1H), 7.66-7.75 (m, 2H), 7.49 (d, J=8.29 Hz, 2H), 7.29-7.39 (m, 6H), 5.06 (s, 2H), 3.98 (s, 2H), 2.83 (s, 5H), 2.17 (d, J=6.75 Hz, 2H), 1.86-2.04 (m, 2H), 1.73 (d, J=9.82 Hz, 5H), 1.55-1.65 (m, 1H), 1.44-1.54 (m, 1H), 0.90-1.05 (m, 2H).

Example 13

2-(4-(1-(4-morpholin-4-yl-benzyl)piperidin-3-yl)phenyl)-1H-benzimidazole-4-carboxamide This compound was prepared by substituting 4-morpholin-4-yl-benzaldehyde for formaldehyde in EXAMPLE 8. $^1$H NMR (DMSO-$d_6$) δ 9.32 (s, 1H), 8.14 (d, J=8.42 Hz, 2H), 7.85 (d, J=7.49 Hz 1H), 7.72 (d, J=8.11 Hz, 2H), 7.45 (d, J=8.42 Hz, 2H), 7.33 (t, J=7.80 Hz, 1H), 7.15 (d, J=8.42 Hz, 1H), 6.88 (d, J=8.73 Hz, 1H), 3.69-3.74 (m, 4H), 3.05-3.09 (m, 4H), 2.81-2.88 (m, 4H), 1.97-2.06 (m, 2H), 1.72 (dt, J=6.55, 3.28 Hz, 1H), 1.56-1.65 (m, 2H), 1.49 (td, J=11.93, 3.90 Hz, 1H).

Example 14

2-(4-(1-(4-piperidin-1-ylbenzyl)piperidin-3-yl)phenyl)-1H-benzimidazole-4-carboxamide This compound was prepared by substituting 4-piperidin-1-yl-benzaldehyde for acetaldehyde in EXAMPLE 8. $^1$H NMR (DMSO-$d_6$) δ 9.30 (s, 1H), 8.14 (d, J=8.42 Hz, 2H), 7.85 (d, J=7.49 Hz 1H), 7.68-7.74 (m, 2H), 7.45 (d, J=8.42 Hz, 2H), 7.32 (t, J=7.64 Hz, 1H), 7.12 (d, J=8.42 Hz, 2H), 6.85 (d, J=8.73 Hz, 2H), 3.22 (m, 2H), 3.07 (m, 2H), 2.84 (d, J=13.41 Hz, 3H), 1.97-2.01 (m, 1H), 1.74 (m, 1H), 1.55-1.64 (m, 5H), 1.46-1.55 (m, 3H), 1.22-1.26 (m, 1H).

Example 15

2-(4-(1-piperidin-4-ylmethyl-piperidin-3-yl)phenyl)-1H-benzimidazole-4-carboxamide A mixture of EXAMPLE 12 (0.057 g) and 20% Pd(OH)$_2$/C (0.01 g) in ethanol (5 mL) and acetic acid (0.5 mL), was stirred under hydrogen for 18 hours, filtered and concentrated. The concentrate was purified by chromatography on silica gel with 10% methanol/dichloromethane. $^1$H NMR (DMSO-$d_6$) δ 9.33 (s, 1H), 8.16 (d, J=8.29 Hz, 2H), 7.84 (d, J=7.67 Hz 2H), 7.72 (d, J=7.98 Hz, 2H), 7.48 (d, J=8.29 Hz, 2H), 7.31 (t, J=7.67 Hz, 1H), 3.17 (s, 2H), 2.89-2.94 (m, 3H), 2.83-2.88 (m, 3H), 2.46 (s, 1H), 2.14 (d, J=7.06 Hz, 2H), 2.02 (t, J=10.13 Hz, 1H), 1.50-1.73 (m, 5H), 1.44-1.54 (m, 1H), 0.95-1.05 (m, 2H).

Example 16

2-(4-(1-ethyl-piperidin-4-yl)phenyl)-1H-benzimidazole-4-carboxamide

This compound was prepared by substituting EXAMPLE 1 for EXAMPLE 2 in EXAMPLE 4. $^1$H NMR (DMSO-$d_6$) δ 9.34 (s, 1H), 8.22 (d, J=8.29 Hz, 2H), 7.87 (d, J=7.36 Hz, 2H), 7.77 (d, J=7.67 Hz, 2H), 7.48 (d, J=7.67 Hz, 2H), 7.35 (t, J=7.67 Hz, 1H), 3.49-3.59 (m, 2H), 3.14-3.19 (m, 2H), 2.90-3.07 (m, 2H), 2.06-2.12 (m, 2H), 1.91 (d, J=5.52 Hz, 3H), 1.27 (t, J=7.21 Hz, 3H), 1.20 (d, J=7.36 Hz, 1H).

Example 17 tert-butyl 4-(4-(4-carbamoyl-1H-benzimidazol-2-yl) piperidine-1-carboxylate

A solution of the product of EXAMPLE 1 (0.085 g), di-tert-butyldicarbonate (0.25 g), triethylamine (0.2 mL) and 4-dimethylaminopyridine (catalytic), in dichloromethane (2 mL) was stirred at ambient temperature for 72 hours and concentrated. The concentrate was purified by chromatography on silica gel with 7% methanol/dichloromethane. $^1$H NMR (DMSO-$d_6$) δ 8.17 (d, J=8.29 Hz, 2H), 7.85 (d, J=7.67 Hz, 1H), 7.72 (d, J=7.98 Hz, 2H), 7.47 (d, J=8.59 Hz, 2H), 7.32 (t, J=7.83 Hz, 1H), 4.06-4.12 (m, 2H), 2.74-2.92 (m, 2H), 1.75-1.85 (m, 2H), 1.55 (dd, J=12.43, 3.84 Hz, 2H), 1.43 (s, 9H), 1.33-1.39 (m, 2H).

Example 18

2-(4-(1-methyl-piperidin-4-yl)phenyl)-1H-benzimidazole-4-carboxamide

This compound was prepared by substituting EXAMPLE 1 for EXAMPLE 2 in EXAMPLE 3. $^1$H NMR (DMSO-$d_6$) δ 9.35 (d, J=2.75 Hz, 1H), 8.22 (d, J=8.24 Hz, 2H), 7.87 (d, J=7.32 Hz, 1H), 7.73-7.80 (m, 2H), 7.48 (d, J=7.93 Hz, 2H), 7.35 (t, J=7.78 Hz, 1H), 3.51 (s, 2H), 3.11 (s, 1H), 2.94 (s, 1H), 2.83 (s, 3H), 2.05 (s, 2H), 1.91 (s, 2H), 1.23 (s, 1H).

Example 19

2-(4-(1-isopropyl-piperidin-4-yl)phenyl)-1H-benzimidazole-4-carboxamide

This compound was prepared by substituting EXAMPLE 1 for EXAMPLE 2 in EXAMPLE 5. $^1$H NMR (DMSO-$d_6$) δ 8.97 (s, 1H), 8.23 (d, J=8.24 Hz, 2H), 7.87 (d, J=7.63 Hz, 1H), 7.73-7.81 (m, 2H), 7.47 (d, J=8.24 Hz, 2H), 7.36 (t, J=7.78 Hz, 1H), 3.53 (d, J=9.46 Hz, 1H), 3.26 (s, 1H), 3.10-3.16 (m, 3H), 3.00 (ddd, J=12.13, 8.77, 3.81 Hz, 1H), 2.11 (d, J=13.73 Hz, 2H), 1.91-2.00 (m, 2H), 1.30 (d, J=6.71 Hz, 6H).

Example 20

2-(4-piperidin-4-ylmethylphenyl)-1H-benzimidazole-4-carboxamide

Example 20A tert-butyl 4-(4-(2-amino-3-carbamoylphenylcarbamoyl)benzyl)piperidine-1-carboxylate A solution of (4-(N-Boc-piperidinyl)methyl)-4-benzoic acid (1.1 g) in pyridine (25 mL) and DMF (25 mL) at 40° C. was treated with CDI (587 mg) over 30 minutes then with 2,3-diaminobenzamide dihydrochloride (772 mg), stirred at ambient temperature for 18 hours and concentrated. The concentrate was partitioned between ethyl acetate and dilute aqueous sodium bicarbonate. The solid that precipitated from the bi-phase mixture was collected by filtration, washed with water and ethyl acetate, and dried.

Example 20B 2-(4-piperidin-4-ylmethylphenyl)-1H-benzimidazole-4-carboxamide

A suspension of EXAMPLE 20A in acetic acid at reflux was stirred for 2 hours, cooled and concentrated. The concentrate was dissolved in ethyl acetate, washed with sodium bicarbonate and water and concentrated. The concentrate was flash chromatographed on silica gel with 20% Methanol/ethyl acetate. 1H NMR (DMSO-$d_6$) δ 1.27-1.44 (m, 2H), 1.75 (d, J=13.20 Hz, 2H), 1.82-1.97 (m, 1H), 2.65 (d, J=7.06 Hz, 2H), 2.76-2.92 (m, 2H), 3.26 (d, J=12.89 Hz, 2H), 7.35 (t, J=7.83 Hz, 1H), 7.42 (d, J=8.29 Hz, 2H), 7.74 (d, J=0.92 Hz, 1H), 7.76 (d, J=0.92 Hz, 1H), 7.87 (d, J=6.75 Hz, 1H), 8.18 (d, J=8.29 Hz, 2H), 8.25 (d, J=7.98 Hz, 1H), 8.55 (d, J=11.97 Hz, 1H), 9.26 (s, 1H).

Example 21 tert-butyl 2-(4-(4-carbamoyl-1H-benzimidazol-2-yl) phenyl)pyrrolidine-1-carboxylate N-Boc-4-pyrrolidin-2-ylbenzoic acid (0.29 g) in dimethylformamide (DMF, 1 mL) and pyridine (1 mL) at 40° C. was stirred for 10 minutes, treated with CDI (0.17 g) stirred for 30 minutes, treated with 2,3-diaminobenzamide dihydrochloride (0.22 g), stirred at ambient temperature for 3.5 hours, treated with isopropanol (2 mL), stirred at ambient temperature for 16 hours, treated with isopropanol (5 mL) and hexanes (40 mL) and decanted. The residue was stirred in water (3 mL) at ambient temperature with 2 drops 50% NaOH for 5 hours and filtered. The filtrant was stirred in acetic acid (3 mL) at reflux for 7.5 hours, cooled and concentrated. The concentrate was stirred in dichloromethane (5 mL) and hexane (15 mL) and filtered. $^1$H NMR (DMSO-$d_6$) δ 13.35 (br, 1H), 9.35 (br, 1H), 8.18 (br d, J=7.8 Hz, 2H), 7.87 (d, J=7.4 Hz, 1H), 7.75 (br, 1H), 7.72 (d, J=8.2 Hz, 1H), 7.40 (br d, J=8.5 Hz, 2H), 7.34 (t, J=7.8 Hz, 1H), 4.79 (brm, 1H), 3.55 (m, 2H), 2.36 (m, 1H), 1.80 (m, 3H), 1.41 (s, 4H), 1.12 (s, 5H).

Example 22

2-(4-(2-Piperidin-2-yl-ethyl)phenyl)-1H-benzimidazole-4-carboxamide

Example 22A 2-(4-bromo-2-chlorophenyl)-1H-benzimidazole-4-carboxamide

To 4-bromo-2-chlorobenzoic acid (2.48 g) in pyridine (12 mL) and DMF (12 mL) was added CDI (1.88 g). The solution was stirred at 45° C. for 2 hours, cooled, treated with 2,3-diaminobenzamide dihydrochloride (2.36 g), stirred at ambient temperature for 18 hours, and concentrated. The concentrate was partitioned between ethyl acetate (70 mL) and water (100 mL) and filtered. The filtrant was washed with water and ethyl acetate and dried. This solid was suspended in acetic acid (40 mL) and the mixture was heated at 125° C. for 4 hours and filtered. The filtrate was cooled to ambient temperature and filtered. The filtrant was washed with methanol and dried to give the first batch of product. The mother liquor was concentrated and the concentrate was treated with dichloromethane and filtered to provide a second batch of solid.

Example 22B 2-(2-chloro-4-(2-pyridin-2-yl-vinyl)phenyl)-1H-benzimidazole-4-carboxamide To EXAMPLE 22A (200 mg), $Pd_2(dba)_3$ (palladium dibenzylideneacetone, 52 mg) and tri-o-tolylphosphine (52 mg) was added DMF (10 mL), 2-vinylpyridine (123 μL) and triethylamine (238 μL). The mixture was purged with nitrogen and stirred at 80° C. for 18 hours, cooled to ambient temperature, filtered through a membrane filter and concentrated. The concentrate was purified by HPLC (Zorbax, C-18, 250×2.54 column, mobile phase A: 0.1% TFA in water; B: 0.1% TFA in $CH_3CN$; 0-100% gradient).

Example 22C 2-(4-(2-pyridin-2-yl-ethyl)phenyl)-1H-benzimidazole-4-carboxamide To EXAMPLE 22B (100 mg) in a mixture of methanol (10 mL) and dichloromethane (4 mL) was added 10% Pd/C (30 mg) under nitrogen. This suspension was purged with hydrogen and was stirred under hydrogen (balloon) for 4 hours. Solid material was filtered off and the filtrate was concentrated. The concentrate was purified by HPLC (Zorbax, SB C-18, 250×2.54 column, mobile phase A: 0.1% TFA in water; B: 0.1% TFA in $CH_3CN$; 0-100% gradient).

Example 22D 2-(4-(2-piperidin-2-yl-ethyl)phenyl)-1H-benzimidazole-4-carboxamide EXAMPLE 22C (30 mg) in methanol (20 mL) was added of $Pd(OH)_2$/C (50 mg). The reaction mixture was purged with hydrogen, shaken under 60 psi of hydrogen for 18 hours, and filtered. The filtrate was concentrated, and the concentrate was purified by HPLC (Zorbax, C-18, 250×2.54 column, mobile phase A: 0.1% TFA in water; B: 0.1% TFA in $CH_3CN$; 0-100% gradient). $^1$H NMR ($CD_3OD$) δ 1.47-1.62 (m, 3H), 1.66-1.72 (m, 1H), 1.88-1.98 (m, 3H), 1.99-2.07 (m, 1H), 2.14 (d, J=15.26 Hz, 1H), 2.81-2.95 (m, 2H), 3.01 (t, J=12.82 Hz, 1H), 3.11-3.19 (m, 1H), 3.37-3.44 (m, 1H), 7.56 (d, J=7.93 Hz, 2H), 7.57 (t, J=7.78 Hz, 1H), 7.90 (d, J=7.32 Hz, 1H), 8.01 (d, J=7.63 Hz, 1H), 8.15 (d, J=8.54 Hz, 1H).

Example 23

2-(4-(1-isopropylpyrrolidin-3-yl)phenyl)-1H-benzimidazole-4-carboxamide

EXAMPLE 38 (100 mg) in methanol (10 mL) was added acetone (38 mg). The solution was stirred at ambient temperature for 40 minutes, treated with sodium triacetoxyborohydride (253 mg) and acetic acid (100 μL), stirred for 18 hours, treated with dichloromethane and washed with dilute NaOH and water. The organic phase was concentrated and the concentrate was purified by HPLC (Zorbax, C-18, 250×2.54 column, Mobile phase A: 0.1% TFA in water; B: 0.1% TFA in $CH_3CN$; 0-100% gradient). $^1$H NMR ($CD_3OD$) δ 1.44 (d, J=6.71 Hz, 6H), 2.16-2.34 (m, 1H), 2.56-2.63 (m, 1H), 3.24-3.37 (m, 1H), 3.52-3.61 (m, 2H), 3.64-3.73 (m, 1H), 3.77-3.88 (m, 2H), 4.02 (dd, J=10.68, 7.02 Hz, 1H), 7.54 (t, J=7.93 Hz, 1H), 7.65 (d, J=7.93 Hz, 2H), 7.88 (d, J=7.63 Hz, 1H), 7.99 (d, J=7.63 Hz, 1H), 8.19 (d, J=7.93 Hz, 2H).

Example 24

2-(4-(1-cyclopentylpyrrolidin-3-yl)phenyl)-1H-benzimidazole-4-carboxamide

This compound was prepared according to the procedure for EXAMPLE 23 and substituting cyclopentanone for acetone. 1H NMR ($CD_3OD$) δ 1.68-1.91 (m, 6H), 2.15-2.25 (m, 2H), 2.28-2.37 (m, 1H), 2.55-2.63 (m, 1H), 3.26-3.33 (m, 1H), 3.49-3.55 (m, 1H), 3.67-3.77 (m, 2H), 3.82-3.94 (m, 2H), 4.06 (dd, J=10.68, 7.02 Hz, 1H), 7.53 (t, J=7.78 Hz, 1H), 7.64 (d, J=7.63 Hz, 2H), 7.88 (d, J=7.32 Hz, 1H), 7.99 (d, J=7.63 Hz, 1H), 8.18 (d, J=7.93 Hz, 2H).

Example 25

2-(4-(1-cyclohexylpyrrolidin-3-yl)phenyl)-1H-benzimidazole-4-carboxamide

This compound was prepared according to the procedure for EXAMPLE 23 and substituting cyclohexanone for acetone. $^1$H NMR ($CD_3OD$) δ 1.16-1.36 (m, 3H), 1.41-1.52 (m, 2H), 1.66 (d, J=12.82 Hz, 1H), 1.79-1.92 (m, 2H), 2.01 (d, J=12.21 Hz, 1H), 2.09-2.15 (m, J=11.60 Hz, 1H), 2.23-2.35 (m, 3H), 2.55-2.63 (m, 1H), 3.12-3.20 (m, 1H), 3.49-3.56 (m, 1H), 3.69-3.77 (m, 1H), 4.80 (t, J=7.93 Hz, 1H), 7.47 (t, J=7.93 Hz, 1H), 7.80 (d, J=8.24 Hz, 2H), 7.84 (d, J=7.63 Hz, 1H), 7.99 (d, J=7.63 Hz, 1H), 8.33 (d, J=8.24 Hz, 2H).

Example 26

2-(2-fluoro-4-piperidin-4-ylphenyl)-1H-benzimidazole-4-carboxamide

Example 26A 2-(4-bromo-2-fluorophenyl)-1H-benzimidazole-4-carboxamide

4-Bromo-2-fluorobenzoic acid (5 g) in a mixture of pyridine (50 mL) and DMF (50 mL) at 45° C. was treated with CDI (0.856 g), stirred at 45° C. for 1 hour, treated with 2,3-diaminobenzamide dihydrochloride (5.1 g), stirred at ambient temperature for 18 hours and concentrated. The concentrate was dissolved in acetic acid (100 mL), heated at 70° C. for 1 hour and concentrated. The concentrate was partitioned between ethyl acetate and sodium bicarbonate solution and the organic phase was isolated, washed with brine and concentrated. The concentrate was flash chromatographed on silica gel with ethyl acetate.

Example 26B 2-(2-fluoro-4-pyridin-4-ylphenyl)-1H-benzimidazole-4-carboxamide EXAMPLE 26A (200 mg), $Pd_2(dba)_3$ (55 mg) and tri-o-tolylphosphine (55 mg) was added DMF (10 mL), 4-(tri-n-butylstannyl)pyridine (220 mg) and triethylamine (238 μL). The mixture was purged with nitrogen, heated at 75° C. for 18 hours, cooled and flash chromatographed on silica gel with (5% Methanol/20% ethyl acetate/75% hexanes). Product was recrystallized from methanol.

Example 26C

2-(2-fluoro-4-piperidin-4-ylphenyl)-1H-benzimidazole-4-carboxamide

EXAMPLE 26B (80 mg) and catalytic 5% Pt/C in methanol (10 mL) was hydrogenated under 60 psi of hydrogen until starting material was consumed and filtered. The filtrate was concentrated and the concentrate purified by HPLC (Zorbax, C-18, 250×2.54 column, mobile phase A: 0.1% TFA in water; B: 0.1% TFA in $CH_3CN$; 0-100% gradient). $^1$H NMR ($CD_3OD$) δ 1.93-2.02 (m, 2H), 2.15 (d, J=14.04 Hz, 2H), 3.03-3.10 (m, 1H), 3.14-3.22 (m, 2H), 3.55 (d, J=12.82 Hz, 2H), 7.32-7.40 (m, 2H), 7.52 (t, J=7.93 Hz, 1H), 7.90 (d, J=7.93 Hz, 1H), 8.01 (d, J=7.63 Hz, 1H), 8.21 (t, J=7.78 Hz, 1H).

Example 27

2-(2-fluoro-4-piperidin-3-ylphenyl)-1H-benzimidazole-4-carboxamide

This compound was prepared according to the procedure for EXAMPLE 26 and substituting 3-(tri-n-butylstannyl)pyridine for 4-(tri-n-butylstannyl)pyridine. $^1$H NMR ($CD_3OD$) δ 1.83-1.97 (m, 2H), 2.07-2.13 (m, 2H), 3.04-3.10 (m, 1H), 3.14-3.21 (m, 2H), 3.45-3.55 (m, 2H), 7.38-7.41 (m, 2H), 7.50 (t, J=7.78 Hz, 1H), 7.88 (d, J=7.93 Hz, 1H), 8.00 (d, J=7.63 Hz, 1H), 8.22 (t, J=8.09 Hz, 1H).

Example 28

2-(4-(1-isopropylpiperidin-4-ylmethyl)phenyl)-1H-benzimidazole-4-carboxamide A solution of EXAMPLE 19 (50 mg) in acetone and 1,2-dichloroethane (5 mL) was stirred for 40 minutes, treated with sodium triacetoxyborohydride (63 mg) and acetic acid (43 μL), stirred for 18 hours and concentrated. The concentrate was purified by HPLC (Zorbax C-8, 0.1% TFA/$CH_3CN$/water). $^1$H NMR ($CD_3OD$) δ 1.34 (d, J=6.75 Hz, 6H), 1.52-1.61 (m, 2H), 1.97-2.00 (m, 3H), 2.76 (d, J=6.44 Hz, 2H), 3.00 (t, J=11.97 Hz, 2H), 3.40-3.54 (m, 3H), 7.46-7.56 (m, 3H), 7.86 (d, J=7.98 Hz, 1H), 7.99 (d, J=7.67 Hz, 1H), 8.14 (d, J=8.29 Hz, 2H).

Example 29

2-(4-(1-isopropylpyrrolidin-2-yl)phenyl)-1H-benzimidazole-4-carboxamide

This compound was prepared according to the procedure for EXAMPLE 23 and substituting EXAMPLE 33 for EXAMPLE 38. $^1$H NMR ($CD_3OD$) δ 1.34 (dd, J=6.56, 1.98 Hz, 6H), 2.23-2.37 (m, 3H), 2.56-2.64 (m, 1H), 3.45-3.56 (m, 2H), 3.66-3.74 (m, 1H), 4.71-4.77 (m, 1H), 7.49 (t, J=7.93 Hz, 1H), 7.81-7.86 (m, 3H), 7.99 (d, J=7.63 Hz, 1H), 8.32 (d, J=8.54 Hz, 2H).

Example 30

2-(4-(1-cyclopropylmethylpyrrolidin-3-yl)phenyl)-1H-benzimidazole-4-carboxamide This compound was prepared according to the procedure for EXAMPLE 23 and substituting cyclopropylcarboxaldehyde for acetone. 1H NMR ($CD_3OD$) δ 0.46-0.51 (m, 2H), 0.74-0.79 (m, 2H), 1.16-1.24 (m, 1H), 2.18-2.38 (m, 1H), 2.56-2.65 (m, 1H), 3.17-3.38 (m, 2H), 3.46-3.54 (m, 1H), 3.71-3.78 (m, 1H), 3.85-3.94 (m, 1H), 3.95-4.02 (m, 1H), 4.09-4.14 (m, 1H), 7.54 (t, J=7.93 Hz, 1H), 7.65 (d, J=8.24 Hz, 2H), 7.88 (d, J=7.63 Hz, 1H), 7.99 (d, J=7.63 Hz, 1H), 8.19 (d, J=7.93 Hz, 2H).

Example 31

2-(4-(1-cyclopentylpyrrolidin-2-yl)phenyl)-1H-benzimidazole-4-carboxamide

This compound was prepared according to the procedure for EXAMPLE 24 and substituting EXAMPLE 33 for EXAMPLE 38. $^1$H NMR ($CD_3OD$) δ 1.33-1.43 (m, 1H), 1.54-1.91 (m, 6H), 2.14-2.19 (m, 1H), 2.28-2.37 (m, 3H), 2.59-2.66 (m, 1H), 3.46-3.52 (m, 1H), 3.67-3.74 (m, 1H), 3.81-3.87 (m, 1H), 4.68 (t, J=7.93 Hz, 1H), 7.48 (t, J=7.93 Hz, 1H), 7.81 (d, J=8.24 Hz, 2H), 7.85 (d, J=8.24 Hz, 1H), 8.00 (d, J=7.63 Hz, 1H), 8.32 (d, J=8.24 Hz, 2H).

Example 32

2-(4-(1-cyclohexylpyrrolidin-2-yl)phenyl)-1H-benzimidazole-4-carboxamide

This compound was prepared according to the procedure for EXAMPLE 25 and substituting EXAMPLE 33 for EXAMPLE 38. $^1$H NMR ($CD_3OD$) δ 1.16-1.36 (m, 3H), 1.41-1.52 (m, 2H), 1.66 (d, J=12.82 Hz, 1H), 1.83 (dd, J=13.12, 1.83 Hz, 1H), 1.90 (d, J=13.12 Hz, 1H), 2.01 (d, J=12.21 Hz, 1H), 2.12 (d, J=11.60 Hz, 1H), 2.24-2.35 (m, 3H), 2.55-2.63 (m, 1H), 3.12-3.20 (m, 1H), 3.48-3.55 (m, 1H), 3.70-3.77 (m, 1H), 4.80 (t, J=7.93 Hz, 1H), 7.47 (t, J=7.93 Hz, 1H), 7.80 (d, J=8.24 Hz, 2H), 7.84 (d, J=7.63 Hz, 1H), 7.99 (d, J=7.63 Hz, 1H), 8.33 (d, J=8.24 Hz, 2H).

Example 33

2-(4-pyrrolidin-2-ylphenyl)-1H-benzimidazole-4-carboxamide

EXAMPLE 21 (0.23 g) in 1M HCl in ethanol (5 mL) was stirred for 19 hours, treated with 12M HCl (0.5 mL), stirred for 19 hours, treated with 12M HCl (0.5 mL), stirred for 6 hours and concentrated. The concentrate was flash chromatographed on silica gel using 95:5:1 to 80:20:1 dichloromethane/methanol/$NH_4OH$. $^1$H NMR (DMSO-$d_6$) δ 9.34 (br, 1H), 8.17 (d, J=8.4 Hz, 2H), 7.85 (d, J=7.4 Hz, 1H), 7.74 (br, 1H), 7.73 (d, J=7.1 Hz, 1H), 7.59 (d, J=7.8 Hz, 2H), 7.33 (t, J=7.8 Hz, 1H), 4.18 (t, J=7.6 Hz, 1H), 3.01 (m, 2H), 2.20 (m, 1H), 1.80 (m, 2H), 1.56 (m, 1H).

Example 34

2-(4-(1-propylpyrrolidin-3-yl)phenyl)-1H-benzimidazole-4-carboxamide

This compound was prepared according to the procedure for EXAMPLE 23 and substituting propionaldehyde for acetone. 1H NMR ($CD_3OD$) δ 1.06 (t, J=7.48 Hz, 3H), 1.77-1.86 (m, 2H), 2.17-2.38 (m, 1H), 2.55-2.64 (m, 1H), 3.24-3.34 (m, 2H), 3.42-3.50 (m, 1H), 3.67-3.75 (m, 2H), 3.83-3.95 (m, 1H), 4.06 (dd, J=10.37, 7.32 Hz, 1H), 7.51 (t, J=7.78

Hz, 1H), 7.64 (d, J=7.02 Hz, 2H), 7.86 (d, J=7.63 Hz, 1H), 7.99 (d, J=7.63 Hz, 1H), 8.20 (d, J=7.93 Hz, 2H).

Example 35

2-(4-(1-cyclopropylmethylpyrrolidin-2-yl)phenyl)-1H-benzimidazole-4-carboxamide

This compound was prepared according to the procedure for EXAMPLE 30 and substituting EXAMPLE 33 for EXAMPLE 38. $^1$H NMR (CD$_3$OD) δ 0.24 (dd, J=8.70, 3.81 Hz, 1H), 0.34-0.41 (m, 1H), 0.63-0.70 (m, 2H), 0.98-1.07 (m, 1H), 2.31-2.38 (m, 3H), 2.58-2.66 (m, 1H), 2.98-3.08 (m, 2H), 3.42-3.48 (m, 1H), 4.01-4.07 (m, 1H), 4.53-4.60 (m, 1H), 7.46 (t, J=7.78 Hz, 1H), 7.78 (d, J=8.24 Hz, 2H), 7.83 (d, J=7.32 Hz, 1H), 7.99 (d, J=6.71 Hz, 1H), 8.32 (d, J=8.24 Hz, 2H).

Example 36

2-(4-(1-propylpyrrolidin-2-yl)phenyl)-1H-benzimidazole-4-carboxamide

This compound was prepared according to the procedure for EXAMPLE 34 and substituting EXAMPLE 33 for EXAMPLE 38. $^1$H NMR (CD$_3$OD) δ 0.93 (t, J=7.32 Hz, 3H), 1.58-1.64 (m, 1H), 1.70-1.78 (m, 1H), 2.30-2.39 (m, 3H), 2.59-2.64 (m, 1H), 3.03-3.12 (m, 2H), 3.33-3.40 (m, 1H), 3.89-3.95 (m, 1H), 4.53-4.58 (m, 1H), 7.43-7.48 (m, 1H), 7.78 (d, J=8.24 Hz, 2H), 7.83 (d, J=7.32 Hz, 1H), 7.99 (d, J=7.63 Hz, 1H), 8.33 (d, J=8.54 Hz, 2H).

Example 37

2-(2-fluoro-4-piperidin-2-ylphenyl)-1H-benzimidazole-4-carboxamide

This compound was prepared according to the procedure for EXAMPLE 26 and substituting 2-(tri-n-butylstannyl)pyridine for 4-(tri-n-butylstannyl)pyridine. 1H NMR (CD$_3$OD) δ 1.77-1.87 (m, 2H), 1.97-2.10 (m, 3H), 2.18 (d, J=15.87 Hz, 1H), 3.24 (t, J=10.0, 1H), 3.54 (d, J=12.82 Hz, 1H), 4.37-4.42 (m, 1H), 7.44 (t, J=7.93 Hz, 1H), 7.51-7.54 (d, J=10.0, 2H), 7.85 (d, J=7.93 Hz, 1H), 7.99 (d, J=7.63 Hz, 1H), 8.44 (t, J=7.78 Hz, 1H).

Example 38

3-(4-pyrrolidin-2-ylphenyl)-1H-benzimidazole-4-carboxamide

This compound was prepared as described in EXAMPLES 21 and 33, using N-Boc-4-pyrrolidin-3-ylbenzoic acid in place of N-Boc-4-pyrrolidin-2-ylbenzoic acid. $^1$H NMR (DMSO-d$_6$) δ 9.29 (br, 1H), 8.19 (d, J=8.5 Hz, 2H), 7.86 (d, J=7.4 Hz, 1H), 7.75 (br, 1H), 7.73 (d, J=7.9 Hz, 1H), 7.52 (d, J=8.5 Hz, 2H), 7.33 (t, J=7.8 Hz, 1H), 3.32-3.46 (m, 2H), 3.22 (m, 1H), 3.09 (m, 1H), 2.89 (m, 1H), 2.28 (m, 1H), 1.86 (m, 1H).

Example 39

2-(4-(1-methylpyrrolidin-2-yl)phenyl)-1H-benzimidazole-4-carboxamide

This compound was prepared according to the procedure for EXAMPLE 23 and substituting EXAMPLE 33 for EXAMPLE 38 and formaldehyde for acetone. 1H NMR (CD$_3$OD) δ 2.28-2.45 (m, 3H), 2.58-2.66 (m, 1H), 2.84 (s, 3H), 3.31-3.39 (m, 1H), 3.89-3.95 (m, 1H), 4.46-4.52 (m, 1H), 7.44-7.48 (m, 1H), 7.78 (d, J=8.24 Hz, 2H), 7.82 (d, J=8.24 Hz, 1H), 7.98 (d, J=7.63 Hz, 1H), 8.31 (d, J=8.54 Hz, 2H).

Example 40

2-(4-(1-methylpyrrolidin-3-yl)phenyl)-1H-benzimidazole-4-carboxamide

This compound was prepared according to the procedure for EXAMPLE 23 and substituting formaldehyde for acetone. $^1$H NMR (CD$_3$OD) δ 2.19-2.39 (m, 1H), 2.56-2.65 (m, 1H), 3.06 (s, 3H), 3.23-3.46 (m, 1H), 3.63-3.80 (m, 2H), 3.85-4.07 (m, 2H), 7.52 (t, J=7.93 Hz, 1H), 7.62 (d, J=7.93 Hz, 2H), 7.86 (d, J=7.93 Hz, 1H), 7.98 (d, J=7.63 Hz, 1H), 8.17 (d, J=8.24 Hz, 2H).

Example 41

2-(2-fluoro-4-(1-isopropylpiperidin-3-yl)phenyl)-1H-benzimidazole-4-carboxamide

This compound was prepared according to the procedure for EXAMPLE 23 and substituting EXAMPLE 27 for EXAMPLE 38. $^1$H NMR (CD$_3$OD) δ 1.41 (d, J=6.41 Hz, 3H), 1.42 (d, J=6.41 Hz, 3H), 1.79-2.18 (m, 4H), 3.05-3.13 (m, 1H), 3.19-3.33 (m, 2H), 3.52-3.67 (m, 3H), 7.39-7.46 (m, 2H), 7.53 (t, J=7.78 Hz, 1H), 7.90 (d, J=8.24 Hz, 1H), 8.01 (d, J=7.63 Hz, 1H), 8.21 (t, J=7.93 Hz, 1H).

Example 42

2-(4-piperidin-3-yl-3-trifluoromethylphenyl)-1H-benzimidazole-4-carboxamide

This compound was prepared according to the procedure for EXAMPLE 26 and substituting 4-bromo-3-trifluoromethylbenzoic acid for 4-bromo-2-fluorobenzoic acid. $^1$H NMR (CD$_3$OD) δ 1.89-2.20 (m, 3H), 2.97 (s, 1H), 3.11-3.20 (m, 1H), 3.32-3.66 (m, 4H), 7.44-7.49 (m, 1H), 7.83 (d, J=8.24 Hz, 1H), 7.90 (dd, J=11.90, 8.24 Hz, 1H), 7.98 (d, J=7.63 Hz, 1H), 8.46 (d, J=8.24 Hz, 1H), 8.54 (s, 1H).

Example 43

2-(2-fluoro-4-(1-methylpiperidin-3-yl)phenyl)-1H-benzimidazole-4-carboxamide

This compound was prepared according to the procedure for EXAMPLE 23 and substituting EXAMPLE 27 for EXAMPLE 38 and formaldehyde for acetone. 1H NMR (CD$_3$OD) δ 1.75-1.83 (m, 1H), 1.93-2.01 (m, 1H), 2.07-2.15 (m, 2H), 2.94 (s, 3H), 3.02-3.07 (m, 1H), 3.14-3.22 (m, 2H), 3.30-3.33 (m, 1H), 3.58-3.66 (m, 2H), 7.32-7.37 (m, 2H), 7.44 (t, J=7.78 Hz, 1H), 7.84 (d, J=8.24 Hz, 1H), 7.98 (d, J=7.63 Hz, 1H), 8.25-8.29 (m, 1H).

Example 44

6-chloro-2-(4-pyrrolidin-2-ylphenyl)-1H-benzimidazole-4-carboxamide

Example 44A 2-amino-5-chloro-3-nitrobenzamide

A solution of 2-amino-3-nitrobenzamide (5 g) in acetonitrile (1250 mL) at 60° C. was treated with N-chlorosuccinimide (3.87 g), stirred for 24 hours, cooled and filtered.

Example 44B 2,3-diamino-5-chlorobenzamide

To a solution of EXAMPLE 44A (4 g) in THF (500 mL) and ethanol (500 mL) was added 50% Raney nickel in water (2 g). The reaction mixture was stirred under hydrogen (balloon) for 6 hours and filtered.

Example 44C tert-butyl 2-(4-(4-Carbamoyl-6-chloro-1H-benzimidazol-2-yl)phenyl)pyrrolidine-1-carboxylate A solution of tert-butyl 2-(4-carboxyphenyl)-pyrrolidine-1-carboxylate (500 mg) in dichloromethane (10 mL) was treated with oxalyl chloride (0.15 mL) and DMF (1 drop), stirred for 1 hour and concentrated. The concentrate was dissolved in dichloromethane, and this solution was added to EXAMPLE 44B (316 mg) in THF (10 mL), treated with triethylamine (2 mL), stirred for 18 hours and concentrated. The concentrate was dissolved in acetic acid (10 mL), heated at 80° C. for 2 hours and concentrated. The concentrate was dissolved in ethyl acetate, washed with sodium bicarbonate solution and brine and concentrated. The concentrate was flash chromatographed on silica gel with ethyl acetate.

Example 44D 6-chloro-2-(4-pyrrolidin-2-ylphenyl)-1H-benzimidazole-4-carboxamide A solution of EXAMPLE 44C (410 mg) in dichloromethane (20 mL) was treated with TFA (4 mL), stirred for 1 hour and concentrated. The concentrate was purified by HPLC (Zorbax, C-18, 250×2.54 column, mobile phase A: 0.1% TFA in water; B: 0.1% TFA in $CH_3CN$; 0-100% gradient). $^1$H NMR (DMSO-$d_6$) δ 2.04-2.20 (m, 3H), 2.41-2.52 (m, 2H), 3.33-3.46 (m, 2H), 4.65-4.71 (m, 1H), 7.72 (d, J=8.29 Hz, 2H), 7.81-7.84 (m, 1H), 7.95 (s, 1H), 8.34 (d, J=8.29 Hz, 2H), 8.94 (s, 1H), 9.14 (s, 1H), 9.73 (s, 1H).

Example 45

6-Fluoro-2-(4-pyrrolidin-2-ylphenyl)-1H-benzimidazole-4-carboxamide

Example 45A

2-Bromo-4-fluoro-6-nitrophenylamine

To a solution of 4-fluoro-2-nitroaniline (20 g) in a mixture of dichloromethane (600 mL) and acetic acid (200 mL) was slowly added bromine (13 mL) at 0° C. The reaction mixture was stirred at 0° C. for 1 hour and at ambient temperature for 16 hours. The reaction mixture was concentrated and the concentrate partitioned between ethyl acetate (500 mL) and sodium bicarbonate solution (500 mL). The organic phase was washed with sodium bisulphite solution (400 mL) and concentrated. The concentrate was recrystallized from hexanes containing some dichloromethane.

Example 45B 2-amino-5-fluoro-3-nitrobenzonitrile

A suspension of EXAMPLE 45A (22.7 g), zinc cyanide (22.6 g) and tetrakis(triphenylphosphine) palladium (7.78 g) in anhydrous DMF (300 mL) was heated at 80° C. for 22 hours. After cooling, the reaction mixture was partitioned between ethyl acetate (500 mL) and brine (500 mL). The organic phase was washed with water and concentrated. Recrystallization of the concentrate from methanol provided EXAMPLE 45B.

Example 45C 2-amino-5-fluoro-3-nitrobenzamide

A suspension of EXAMPLE 45B (13.9 g) in polyphosphoric acid (400 g) was stirred at 115° C. for 3 hours. After cooling, water and dichloromethane were added and the mixture stirred at ambient temperature for 10 minutes. The solid material was collected by filtration and recrystallized from methanol.

Example 45D 2,3-diamino-5-fluorobenzamide

To a solution of EXAMPLE 45C (11.2 g) in a mixture of THF (50 mL) and ethanol (50 mL) was added Raney nickel (50% in water, 11.0 g). The mixture was stirred under hydrogen (60 psi) for 5 hours. Solid material was filtered off and the filtrate was concentrated.

Example 45E 6-fluoro-2-(4-pyrrolidin-2-ylphenyl)-1H-benzimidazole-4-carboxamide This compound was prepared according to the procedure for EXAMPLE 44 and substituting EXAMPLE 45D for EXAMPLE 44B. 1H NMR (DMSO-$d_6$) δ 2.04-2.20 (m, 3H), 2.41-2.53 (m, 1H), 3.32-3.49 (m, 2H), 4.69 (s, 1H), 7.60-7.64 (m, 2H), 7.72 (d, J=8.24 Hz, 2H), 7.99 (s, 1H), 8.33 (d, J=8.24 Hz, 2H), 8.96 (s, 1H), 9.21 (s, 1H), 9.77 (s, 1H).

Example 46

6-chloro-2-(4-(1-isopropyl-pyrrolidin-2-yl)phenyl)-1H-benzimidazole-4-carboxamide This compound was prepared according to the procedure for EXAMPLE 23 and substituting EXAMPLE 44 for EXAMPLE 38. $^1$H NMR (DMSO-$d_6$) δ 1.23 (d, J=6.41 Hz, 6H), 2.10-2.21 (m, 4H), 2.44-2.49 (m, 1H), 3.35-3.43 (m, 2H), 3.58-3.63 (m, 1H), 4.69 (q, J=8.24 Hz, 1H), 7.81-7.85 (m, 3H), 7.98 (s, 1H), 8.36 (d, J=8.54 Hz, 2H), 9.14 (s, 1H), 9.78 (s, 1H).

Example 47

6-chloro-2-(4-(1-cyclopentyl-pyrrolidin-2-yl)phenyl)-1H-benzimidazole-4-carboxamide This compound was prepared according to the procedure for EXAMPLE 23 and substituting EXAMPLE 44 for EXAMPLE 38 and cyclopentanone for acetone. $^1$H NMR (DMSO-$d_6$) δ 1.23-1.30 (m, 1H), 1.40-1.50 (m, 2H), 1.55-1.67 (m, 2H), 1.70-1.80 (m, 2H), 2.00-2.06 (m, 1H), 2.14-2.21 (m, 4H), 2.47-2.54 (m, 1H), 3.39 (dd, J=11.14, 7.17 Hz, 1H), 3.58-3.65 (m, 1H), 3.72-3.78 (m, 1H), 4.63 (q, J=8.14 Hz, 1H), 7.80-7.84 (m, 3H), 7.99 (s, 1H), 8.35 (d, J=8.54 Hz, 2H), 9.13 (s, 1H), 9.97 (s, 1H).

Example 48

6-Chloro-2-(4-(1-methylpyrrolidin-2-yl)phenyl)-1H-benzimidazole-4-carboxamide

This compound was prepared according to the procedure for EXAMPLE 23 and substituting EXAMPLE 44 for EXAMPLE 38 and formaldehyde for acetone. 1H NMR (DMSO-$d_6$) δ 2.13-2.27 (m, 3H), 2.48-2.53 (m, 1H), 2.73 (d, J=3.36 Hz, 3H), 3.23-3.29 (m, 1H), 3.77-3.82 (m, 1H), 4.44-4.52 (m, 1H), 7.77 (d, J=8.54 Hz, 2H), 7.82 (d, J=1.83 Hz, 1H), 7.84 (d, J=1.83 Hz, 1H), 7.98 (s, 1H), 8.37 (d, J=8.24 Hz, 2H), 9.12 (s, 1H), 10.09 (s, 1H).

Example 49

6-fluoro-2-(4-(1-methylpyrrolidin-2-yl)phenyl)-1H-benzimidazole-4-carboxamide

This compound was prepared according to the procedure for EXAMPLE 23 and substituting EXAMPLE 45 for EXAMPLE 38 and formaldehyde for acetone. 1H NMR (DMSO-$d_6$) δ 2.13-2.29 (m, 3H), 2.48-2.54 (m, 1H), 2.73 (s, 3H), 3.22-3.31 (m, 1H), 3.77-3.84 (m, 1H), 4.45-4.53 (m, 1H), 7.60-7.65 (m, 2H), 7.77 (d, J=8.29 Hz, 2H), 7.96 (s, 1H), 8.35 (d, J=7.98 Hz, 2H), 9.19 (s, 1H), 10.19 (s, 1H).

Example 50

2-(4-(1-ethylpyrrolidin-2-yl)-2-fluorophenyl)-1H-benzimidazole-4-carboxamide

Example 50A methyl 4-bromo-2-fluorobenzoate

To a solution of 4-bromo-2-fluorobenzoic acid (30.8 g) in DMF (150 mL) was added iodomethane (17.5 mL) and powdered sodium hydrogencarbonate (23.5 g). The mixture was stirred for 18 hours and partitioned between ethyl acetate and brine. The organic phase was isolated, washed with dilute sodium bisulfite solution and brine and concentrated. The concentrate was flash chromatographed on silica gel with 7-20% ethyl acetate/hexanes.

Example 50B tert-butyl 2-(3-fluoro-4-methoxycarbonylphenyl)pyrrole-1-carboxylate A mixture of EXAMPLE 50A (4 g), 1-(tert-butoxycarbonyl)pyrrole-2-boronic acid (5.44 g), and dichlorobis(triphenylphosphine)palladium(II) (1.2 g) in 7:3:2 DME/water/ethanol (300 mL) and 2M aqueous $Na_2CO_3$ (17.2 mL) at 80° C. was stirred for 140 minutes, cooled and concentrated. The concentrate was dissolved in ethyl acetate, washed with brine and concentrated. The concentrate was flash chromatographed on silica gel with 1:4 ethyl acetate/hexane.

Example 50C tert-butyl 2-(3-fluoro-4-methoxycarbonylphenyl)pyrrolidine-1-carboxylate A mixture of EXAMPLE 50B (5.5 g) and 5% Pt/C (20 mg) in acetic acid (200 mL) was hydrogenated at 60 psi for 12 hours and filtered. The filtrate was concentrated and the concentrate partitioned between ethyl acetate and sodium bicarbonate solution. The organic phase was isolated and concentrated. The concentrate was flash chromatographed on silica gel with 10-30% ethyl acetate/hexanes.

Example 50D tert-butyl 2-(4-carboxy-3-fluorophenyl)pyrrolidine-1-carboxylate A mixture of EXAMPLE 50C (5.5 g) and lithium hydroxide monohydrate (1.43 g) in THF (50 mL) and water (50 mL) was titrated with methanol until transparent, stirred at ambient temperature for 2 hours, acidified to pH 2 with 2M HCl, concentrated to about 40 mL and filtered.

Example 50E tert-butyl 2-(4-(4-carbamoyl-1H-benzimidazol-2-yl)-3-fluorophenyl)pyrrolidine-1-carboxylate To a solution of EXAMPLE 50D (1.48 g) in pyridine (5 mL) and DMF (5 mL) was added CDI (0.856 g). The solution was stirred at 45° C. for 2 hours, treated with 2,3-diaminobenzamide dihydrochloride (1.08 g), stirred at ambient temperature for 18 hours and concentrated. The concentrate was dissolved in acetic acid (30 mL), and this solution was heated at 80° C. for 3 hours and concentrated. The concentrate was dissolved in ethyl acetate, washed with sodium bicarbonate solution and brine and concentrated. The concentrate was flash chromatographed on silica gel with 0-15% methanol in 2:1 ethyl acetate/hexane.

Example 50F 2-(2-fluoro-4-pyrrolidin-2-ylphenyl)-1H-benzimidazole-4-carboxamide A solution of EXAMPLE 50E (1.5 g) in dichloromethane (50 mL) was treated with TFA (10 mL), stirred for 1 hour and concentrated. The concentrate was purified by HPLC (Zorbax, C-18, 250×2.54 column, mobile phase A: 0.1% TFA in water; B: 0.1% TFA in $CH_3CN$, 0-100% gradient). $^1$H NMR ($CD_3OD$) δ 2.21-2.36 (m, 3H), 2.54-2.63 (m, 1H), 3.47-3.59 (m, 2H), 4.76 (dd, J=9.51, 7.06 Hz, 1H), 7.43 (t, J=7.83 Hz, 1H), 7.50-7.55 (m, 2H), 7.84 (d, J=7.36 Hz, 1H), 7.98 (d, J=7.67 Hz, 1H), 8.42 (t, J=8.13 Hz, 1H).

Example 50G 2-(4-(1-ethylpyrrolidin-2-yl)-2-fluorophenyl)-1H-benzimidazole-4-carboxamide To a solution of EXAMPLE 50F (150 mg) in methanol (6 mL) was added triethylamine (125 mL) and 32 wt/v % acetaldehyde in water (210 mL). The solution was stirred for 1 hour, treated with sodium cyanoborohydride (95 mg), stirred for 3 hours at ambient temperature and at 50° C. for 18 hours and concentrated. The concentrate was purified by HPLC (Zorbax, C-18, 250×2.54 column, mobile phase A: 0.1% TFA in water; B: 0.1% TFA in $CH_3CN$; 0-100% gradient). $^1H$ NMR ($CD_3OD$) δ 1.31-1.36 (m, 3H), 2.30-2.42 (m, 2H), 2.61-2.70 (m, 1H), 3.17-3.29 (m, 2H), 3.34-3.41 (m, 1H), 3.52-3.62 (m, 1H), 3.94-4.01 (m, 1H), 4.64-4.73 (m, 1H), 7.75 (t, J=7.98 Hz, 1H), 7.87 (d, J=7.67 Hz, 1H), 7.93 (d, J=11.35 Hz, 1H), 8.07 (d, J=7.98 Hz, 1H), 8.13 (d, J=7.67 Hz, 1H), 8.28 (t, J=7.52 Hz, 1H).

Example 51

2-(2-fluoro-4-(1-isopropylpyrrolidin-2-yl)phenyl)-1H-benzimidazole-4-carboxamide To a solution of EXAMPLE 50F (80 mg) in methanol (3 mL) was added triethylamine (67 mL) and acetone (35 mL). This solution was stirred at ambient temperature for 1 hour, treated with sodium cyanoborohydride (30 mg), stirred at 50° C. for 18 hours and concentrated. The concentrate was purified by HPLC (Zorbax, C-18, 250×2.54 column, mobile phase A: 0.1% TFA in water; B: 0.1% TFA in $CH_3CN$; 0-100% gradient). $^1H$ NMR ($CD_3OD$) δ 1.33 (d, J=6.71 Hz, 3H), 1.35 (d, J=6.71 Hz, 3H), 2.25-2.34 (m, 3H), 2.58-2.64 (m, 1H), 3.47-3.61 (m, 2H), 3.67-3.74 (m, 1H), 4.72-4.79 (m, 1H), 7.45 (t, J=7.78 Hz, 1H), 7.63 (d, J=8.24 Hz, 1H), 7.66 (d, J=11.90 Hz, 1H), 7.86 (d, J=8.24 Hz, 1H), 8.00 (d, J=7.32 Hz, 1H), 8.48 (t, J=7.78 Hz, 1H).

Example 52

2-(4-(1-Cyclobutylpyrrolidin-2-yl)-2-fluorophenyl)-1H-benzimidazole-4-carboxamide This compound was prepared according to the procedure for EXAMPLE 51 and substituting cyclobutanone for acetone. $^1H$ NMR ($CD_3OD$) δ 1.74-1.82 (m, 3H), 1.93-1.99 (m, 1H), 2.25-2.40 (m, 6H), 2.59-2.65 (m, 1H), 3.76-3.82 (m, 1H), 3.93-3.98 (m, 1H), 4.53-4.57 (m, 1H), 7.46 (t, J=7.78 Hz, 1H), 7.62 (d, J=8.24 Hz, 1H), 7.65 (d, J=11.90 Hz, 1H), 7.86 (d, J=7.93 Hz, 1H), 8.01 (d, J=7.63 Hz, 1H), 8.45 (t, J=7.93 Hz, 1H).

Example 53

2-(2-Fluoro-4-(1-propylpyrrolidin-2-yl)phenyl)-1H-benzimidazole-4-carboxamide

This compound was prepared according to the procedure for EXAMPLE 51 and substituting propionaldehyde for acetone. 1H NMR ($CD_3OD$) δ 0.94 (t, J=7.32 Hz, 3H), 1.61-1.69 (m, 1H), 1.71-1.81 (m, 1H), 2.29-2.37 (m, 3H), 2.62 (m, 1H), 3.04-3.14 (m, 2H), 3.34-3.41 (m, 1H), 3.90-3.96 (m, 1H), 4.53-4.60 (m, 1H), 7.45 (t, J=7.93 Hz, 1H), 7.61 (d, J=8.24 Hz, 1H), 7.64 (d, J=11.90 Hz, 1H), 7.86 (d, J=7.63 Hz, 1H), 8.00 (d, J=7.63 Hz, 1H), 8.46 (t, J=7.78 Hz, 1H).

Example 54

2-(4-(1-cyclopropylmethylpyrrolidin-2-yl)-2-fluorophenyl)-1H-benzimidazole-4-carboxamide This compound was prepared according to the procedure for EXAMPLE 51 and substituting cyclopropanecarboxaldehyde for acetone. 1H NMR ($CD_3OD$) δ 0.24-0.30 (m, 1H), 0.38-0.42 (m, 1H), 0.63-0.71 (m, 2H), 1.00-1.09 (m, 1H), 2.30-2.38 (m, 3H), 2.62-2.67 (m, 1H), 3.01-3.09 (m, 2H), 3.42-3.48 (m, 1H), 4.00-4.07 (m, 1H), 4.59 (t, J=8.39 Hz, 1H), 7.45 (t, J=7.93 Hz, 1H), 7.60 (d, J=8.24 Hz, 1H), 7.62 (d, J=12.21 Hz, 1H), 7.86 (d, J=7.93 Hz, 1H), 8.00 (d, J=7.63 Hz, 1H), 8.47 (t, J=7.78 Hz, 1H).

Example 55

6-fluoro-2-(2-fluoro-4-pyrrolidin-2-ylphenyl)-1H-benzimidazole-4-carboxamide

Example 55A tert-butyl 2-(4-(4-carbamoyl-6-fluoro-1H-benzimidazol-2-yl)-3-fluorophenyl)pyrrolidine-1-carboxylate A solution of EXAMPLE 50D (700 mg) in dichloromethane (8 mL) was treated with oxalyl chloride (296 μL) and DMF (one drop), stirred for 1 hour and concentrated. The concentrate was dissolved in dichloromethane (8 mL), and this solution was added to a solution of EXAMPLE 45D (382 mg) and triethylamine (378 μL) in THF (8 mL). The mixture was stirred for 18 hours and concentrated. The concentrate was dissolved in acetic acid (15 mL), heated at 80° C. for 3 hours and concentrated. The concentrate was partitioned between ethyl acetate and sodium bicarbonate solution the ethyl acetate layer washed with sodium bicarbonate solution and concentrated. The concentrate was flash chromatographed on silica gel with 3:2 ethyl acetate/hexanes.

Example 55B 6-fluoro-2-(2-fluoro-4-pyrrolidin-2-ylphenyl)-1H-benzimidazole-4-carboxamide A solution of EXAMPLE 55A (360 mg) in dichloromethane (25 mL) and trifluoroacetic acid (5 mL) was stirred for 1 hour and concentrated. The concentrate was purified by HPLC (Zorbax, C-18, 250×2.54 column, Mobile phase A: 0.1% TFA in water; B: 0.1% TFA in $CH_3CN$; 0-100% gradient). $^1H$ NMR ($CD_3OD$) δ 2.20-2.37 (m, 3H), 2.56-2.62 (m, 1H), 3.47-3.57 (m, 2H), 4.76 (dd, J=9.31, 7.17 Hz, 1H), 7.50-7.54 (m, 3H), 7.71 (dd, J=10.37, 2.44 Hz, 1H), 8.43 (t, J=7.93 Hz, 1H).

Example 56

6-fluoro-2-(2-fluoro-4-(1-isopropylpyrrolidin-2-yl)phenyl)-1H-benzimidazole-4-carboxamide This compound was prepared according to the procedure for EXAMPLE 23 and substituting EXAMPLE 55 for EXAMPLE 18. $^1H$ NMR ($CD_3OD$) δ 1.36 (dd, J=6.41, 2.44 Hz, 6H), 2.25-2.35 (m, 3H), 2.57-2.65 (m, 1H), 3.45-3.59 (m, 2H), 3.66-3.73 (m, 1H), 4.73-4.77 (m, 1H), 7.52 (dd, J=8.24, 2.44 Hz, 1H), 7.60-7.66 (m, 2H), 7.71 (dd, J=10.53, 2.59 Hz, 1H), 8.47 (t, J=7.93 Hz, 1H).

Example 57

2-(4-(1-Ethylpyrrolidin-2-yl)-2-fluorophenyl)-6-fluoro-1H-benzimidazole-4-carboxamide This compound was prepared according to the procedure for EXAMPLE 50 and substituting EXAMPLE 55 for EXAMPLE 50F. $^1$H NMR (CD$_3$OD) δ 1.31 (t, J=7.21 Hz, 3H), 2.29-2.38 (m, 2H), 2.58-2.68 (m, 1H), 3.11-3.21 (m, 1H), 3.26-3.40 (m, 2H), 3.51-3.78 (m, 1H), 3.88-3.95 (m, 1H), 4.53-4.59 (m, 1H), 7.52 (dd, J=8.13, 2.61 Hz, 1H), 7.56-7.64 (m, 2H), 7.71 (dd, J=10.43, 2.45 Hz, 1H), 8.46 (t, J=7.82 Hz, 1H).

Example 58

6-Fluoro-2-(2-fluoro-4-(1-methylpyrrolidin-2-yl) phenyl)-1H-benzimidazole-4-carboxamide This compound was prepared according to the procedure for EXAMPLE 50 and substituting EXAMPLE 55 for EXAMPLE 50F and formaldehyde for acetaldehyde. $^1$H NMR (CD$_3$OD) δ 2.28-2.43 (m, 3H), 2.61-2.69 (m, 1H), 2.88 (s, 3H), 3.32-3.40 (m, 1H), 3.88-3.96 (m, 1H), 4.48-4.54 (m, 1H), 7.53 (dd, J=8.29, 2.45 Hz, 1H), 7.57-7.63 (m, 2H), 7.72 (dd, J=10.43, 2.46 Hz, 1H), 8.47 (t, J=7.82 Hz, 1H).

Example 59

6-fluoro-2-(2-fluoro-4-piperidin-3-ylphenyl)-1H-benzimidazole-4-carboxamide

Example 59A methyl 2-fluoro-4-pyridin-3-yl-benzoate

A mixture of EXAMPLE 50A (5 g), 3-pyridinylboronic acid (4 g) and dichlorobis(triphenylphosphine)-palladium (II) (1.1 g) in 7:3:2 DME/water/ethanol (200 mL) and 2M aqueous Na$_2$CO$_3$ solution (1 mL) at 80° C. was stirred 18 hours, cooled and filtered. The filtrate was partitioned between ethyl acetate and water, and the ethyl acetate layer washed with water and concentrated. The concentrate was flash chromatographed on silica gel with 1:2 ethyl acetate/hexanes.

Example 59B benzyl 3-(4-methoxycarbonyl-3-fluorophenyl)piperidine-1-carboxylate

EXAMPLE 59A (4.5 g) was hydrogenated with catalytic 5% Pt/C under 60 psi of hydrogen as described for EXAMPLE 26. To a mixture of this product and potassium carbonate (4 g) in dioxane (50 mL) and water (30 mL) was added benzyl chloroformate (2.8 mL). The mixture was stirred at ambient temperature for 4 hours, treated with piperazine, stirred for 30 minutes and concentrated. The concentrate was partitioned between ethyl acetate and dilute hydrochloric acid and the ethyl acetate layer washed with water and concentrated. The concentrate was flash chromatographed on silica gel with 1:2 ethyl acetate/hexanes.

Example 59C benzyl 3-(4-carboxy-3-fluorophenyl)piperidine-1-carboxylate

This compound was prepared according to the procedure for EXAMPLE 50D and substituting EXAMPLE 59B for EXAMPLE 50C.

Example 59D benzyl 3-(4-(4-carbamoyl-6-fluoro-1H-benzimidazol-2-yl)-3-fluorophenyl)piperidine-1-carboxylate A solution of EXAMPLE 59C (1.1 g) in dichloromethane (20 mL) was treated with oxalyl chloride (240 µL) and DMF (one drop), stirred for 1 hour and concentrated. The concentrate was dissolved in dichloromethane (10 mL), and this solution was added into a solution of EXAMPLE 45D (450 mg) and triethylamine (2 mL) in THF (10 mL), stirred at ambient temperature for 18 hours and concentrated. The concentrate was dissolved in acetic acid (15 mL), heated at 80° C. for 3 hours, cooled and concentrated. The concentrate was partitioned between ethyl acetate and sodium bicarbonate solution, and the ethyl acetate layer washed with sodium bicarbonate solution and concentrated. The concentrate was flash chromatographed on silica gel with ethyl acetate.

Example 59E 6-fluoro-2-(2-fluoro-4-piperidin-3-ylphenyl)-1H-benzimidazole-4-carboxamide A solution of EXAMPLE 59D (150 mg) in TFA (10 mL) at 40° C. was stirred for 2.5 days and concentrated. The concentrate was purified by HPLC (Zorbax, C-18, 250×2.54 column, Mobile phase A: 0.1% TFA in water; B: 0.1% TFA in CH$_3$CN; 0-100% gradient). $^1$H NMR (CD$_3$OD) δ 1.83-1.96 (m, 2H), 2.07-2.15 (m, 2H), 3.02-3.21 (m, 3H), 3.44-3.54 (m, 2H), 7.32 (dd, J=4.14, 1.69 Hz, 1H), 7.35 (s, 1H), 7.50 (dd, J=8.29, 2.45 Hz, 1H), 7.69 (dd, J=10.43, 2.45 Hz, 1H), 8.30 (t, J=7.98 Hz, 1H).

Example 60

6-chloro-2-(2-fluoro-4-piperidin-2-ylphenyl)-1H-benzimidazole-4-carboxamide

Example 60A methyl 2-fluoro-4-pyridin-2-yl-benzoate

To a suspension of EXAMPLE 50A (5 g), Pd$_2$(dba)$_3$ (1.5 g) and tri-2-furylphosphine (1.5 g) in DMF (100 mL) was added 2-trimethylstannyl pyridine (9.5 g) and triethylamine (2 mL). The reaction mixture was stirred at 80° C. for 18 hours, cooled and partitioned between ethyl acetate and brine. The ethyl acetate layer was separated and concentrated, and the concentrate flash chromatographed on silica gel with 1:2 ethyl acetate/hexanes.

Example 60B benzyl 2-(4-carboxy-3-fluorophenyl)piperidine-1-carboxylate

This compound was prepared according to the procedure for EXAMPLE 59C and substituting EXAMPLE 60A for EXAMPLE 59A.

Example 60C 6-chloro-2-(2-fluoro-4-piperidin-2-ylphenyl)-1H-benzimidazole-4-carboxamide This compound was prepared according to the procedure for EXAMPLE 59 and substituting EXAMPLE 60B for EXAMPLE 59C and EXAMPLE 44B for EXAMPLE 45D. H NMR (CD$_3$OD) δ 1.77-1.88 (m, 2H), 1.95-2.12 (m, 3H), 2.15-2.22 (m, 1H), 3.19-3.28 (m, 1H), 3.51-3.58 (m, 1H), 4.39 (dd, J=12.27, 2.76 Hz, 1H), 7.51 (d, J=10.13 Hz, 2H), 7.78 (d, J=1.84 Hz, 1H), 7.91 (d, J=2.15 Hz, 1H), 8.44 (t, J=7.82 Hz, 1H).

Example 61

6-fluoro-2-(2-fluoro-4-piperidin-2-ylphenyl)-1H-benzimidazole-4-carboxamide

This compound was prepared according to the procedure for EXAMPLE 60 and substituting EXAMPLE 45D for EXAMPLE 44B. 1H NMR (CD$_3$OD) δ 1.78-1.89 (m, 2H), 1.98-2.09 (m, 3H), 2.15-2.21 (m, 1H), 3.21-3.26 (m, 1H), 3.54 (d, J=12.51 Hz, 1H), 4.39 (dd, J=12.21, 2.44 Hz, 1H), 7.49-7.53 (m, 3H), 7.70 (dd, J=10.37, 2.44 Hz, 1H), 8.43 (t, J=7.78 Hz, 1H).

Example 62

6-fluoro-2-(2-fluoro-4-(1-methylpiperidin-3-yl)phenyl)-1H-benzimidazole-4-carboxamide This compound was prepared according to the procedure for EXAMPLE 50 and substituting EXAMPLE 59 for EXAMPLE 50F and formaldehyde for acetaldehyde H NMR (CD$_3$OD) δ 1.77-1.83 (m, 1H), 1.92-2.02 (m, 1H), 2.09-2.18 (m, 2H), 2.95 (s, 3H), 3.02-3.10 (m, 1H), 3.16-3.21 (m, 2H), 3.61 (d, J=12.21 Hz, 1H), 3.65 (d, J=7.93 Hz, 1H), 7.33 (d, J=4.58 Hz, 1H), 7.34 (s, 1H), 7.50 (dd, J=8.24, 2.44 Hz, 1H), 7.69 (dd, J=10.37, 2.44 Hz, 1H), 8.29 (t, J=7.93 Hz, 1H).

Example 63

2-(4-(1-ethylpiperidin-2-yl)-3-fluorophenyl)-6-fluoro-1H-benzimidazole-4-carboxamide This compound was prepared according to the procedure for EXAMPLE 50 and substituting EXAMPLE 59 for EXAMPLE 50F. 1H NMR (CD$_3$OD) δ 1.40 (t, J=7.32 Hz, 3H), 1.80-1.88 (m, 1H), 1.91-2.02 (m, 1H), 2.08-2.20 (m, 2H), 2.97-3.04 (m, 1H), 3.12-3.21 (m, 1H), 3.26 (q, J=7.32 Hz, 2H), 3.63-3.71 (m, 2H), 7.32-7.37 (m, 2H), 7.50 (dd, J=8.24, 2.44 Hz, 1H), 7.69 (dd, J=10.37, 2.44 Hz, 1H), 8.29 (t, J=7.93 Hz, 1H).

Example 64

6-fluoro-2-(2-fluoro-4-(1-isopropyl-piperidin-3-yl)phenyl)-1H-benzimidazole-4-carboxamide This compound was prepared according to the procedure for EXAMPLE 50 and substituting EXAMPLE 59 for EXAMPLE 50F and acetone for acetaldehyde. $^1$H NMR (CD$_3$OD) δ 1.42 (dd, J=6.56, 3.51 Hz, 6H), 1.79-1.90 (m, 1H), 1.94-2.05 (m, 1H), 2.11 (d, J=13.73 Hz, 1H), 2.18 (d, J=14.65 Hz, 1H), 3.08-3.15 (m, 1H), 3.19-3.26 (m, 2H), 3.51-3.63 (m, 3H), 7.35 (s, 1H), 7.37 (d, J=7.02 Hz, 1H), 7.49 (dd, J=8.24, 2.44 Hz, 1H), 7.68 (dd, J=10.68, 2.44 Hz, 1H), 8.28 (t, J=8.09 Hz, 1H).

Example 65

2-(4-(1-cyclobutylpiperidin-3-yl)-2-fluorophenyl)-6-fluoro-1H-benzimidazole-4-carboxamide This compound was prepared according to the procedure for EXAMPLE 50 and substituting EXAMPLE 59 for EXAMPLE 50F and cyclobutanone for acetaldehyde. $^1$H NMR (CD$_3$OD) δ 1.76-1.97 (m, 4H), 2.14 (t, J=15.71 Hz, 2H), 2.25-2.43 (m, 4H), 2.79-2.87 (m, 1H), 2.99 (t, J=12.36 Hz, 1H), 3.10-3.18 (m, 1H), 3.57 (d, J=11.90 Hz, 2H), 3.66-3.75 (m, 1H), 7.35 (d, J=10.07 Hz, 2H), 7.50 (dd, J=8.24, 2.44 Hz, 1H), 7.70 (dd, J=10.37, 2.44 Hz, 1H), 8.31 (t, J=7.93 Hz, 1H).

Example 67

6-chloro-2-(2-fluoro-4-(1-methylpiperidin-2-yl)phenyl)-1H-benzimidazole-4-carboxamide This compound was prepared according to the procedure for EXAMPLE 50 and substituting EXAMPLE 60 for EXAMPLE 50F and formaldehyde for acetaldehyde. $^1$H NMR (CD$_3$OD) δ 1.73-1.82 (m, 1H), 1.94-2.22 (m, 5H), 2.68 (s, 3H), 3.21-3.28 (m, 1H), 3.69-3.77 (m, 1H), 4.29 (dd, J=11.44, 3.81 Hz, 1H), 7.52-7.57 (m, 2H), 7.76 (d, J=2.14 Hz, 1H), 7.87 (d, J=1.83 Hz, 1H), 8.45 (t, J=7.93 Hz, 1H).

Example 68

6-chloro-2-(4-(1-ethylpiperidin-2-yl)-2-fluorophenyl)-1H-benzimidazole-4-carboxamide This compound was prepared according to the procedure for EXAMPLE 50 and substituting EXAMPLE 60 for EXAMPLE 50F. 1H NMR (CD$_3$OD) δ 1.26 (t, J=7.32 Hz, 3H), 1.75-1.82 (m, 1H), 1.94-2.07 (m, 2H), 2.08-2.21 (m, 3H), 2.92-3.02 (m, 1H), 3.06-3.14 (m, 1H), 3.14-3.22 (m, 1H), 3.80 (d, J=12.82 Hz, 1H), 4.40 (dd, J=11.44, 3.51 Hz, 1H), 7.53-7.58 (m, 2H), 7.77 (d, J=2.14 Hz, 1H), 7.88 (d, J=2.14 Hz, 1H), 8.46 (t, J=7.78 Hz, 1H).

Example 69

6-chloro-2-(4-(1-cyclopropylmethyl-piperidin-2-yl)-2-fluorophenyl)-1H-benzimidazole-4-carboxamide This compound was prepared according to the procedure for EXAMPLE 50 and substituting EXAMPLE 60 for EXAMPLE 50F and cyclopropylaldehyde for acetaldehyde. H NMR (CD$_3$OD) δ 0.21-0.27 (m, 1H), 0.27-0.35 (m, 1H), 0.66-0.79 (m, 2H), 1.00-1.10 (m, 1H), 1.74-1.84 (m, 1H), 1.99-2.09 (m, 2H), 2.09-2.21 (m, 3H), 2.79 (dd, J=13.58, 7.48 Hz, 1H), 2.93 (dd, J=13.58, 6.87 Hz, 1H), 3.23-3.32 (m, 1H), 4.05 (d, J=11.90 Hz, 1H), 4.40 (dd, J=11.14, 3.81 Hz, 1H), 7.51-7.57 (m, 2H), 7.77 (d, J=1.83 Hz, 1H), 7.88 (d, J=1.83 Hz, 1H), 8.47 (t, J=7.93 Hz, 1H).

Example 70

2-(4-(1-ethylpiperidin-2-yl)-2-fluorophenyl)-6-fluoro-1H-benzimidazole-4-carboxamide This compound was prepared according to the procedure for EXAMPLE 50 and substituting EXAMPLE 61 for EXAMPLE 50F. 1H NMR (CD$_3$OD) δ 1.26 (t, J=7.36 Hz, 3H), 1.74-1.84 (m, 1H), 1.92-2.20 (m, 5H), 2.96 (dd, J=13.35, 7.21 Hz, 1H), 3.06-3.14 (m, 1H), 3.14-3.23 (m, 1H), 3.79 (d, J=12.58 Hz, 1H), 4.39 (dd, J=11.20, 3.84 Hz, 1H), 7.50-7.58 (m, 3H), 7.71 (dd, J=10.59, 2.61 Hz, 1H), 8.48 (t, J=7.93 Hz, 1H).

Example 71

2-(4-(1-cyclopropylmethylpiperidin-2-yl)-2-fluorophenyl)-6-fluoro-1H-benzimidazole-4-carboxamide This compound was prepared according to the procedure for EXAMPLE 50 and substituting EXAMPLE 61 for EXAMPLE 50F and cyclopropylaldehyde for acetaldehyde. H NMR (CD$_3$OD) δ 0.21-0.27 (m, 1H), 0.28-0.35 (m, 1H), 0.66-0.78 (m, 2H), 1.01-1.13 (m, 1H), 1.75-1.86 (m, 1H), 1.97-2.20 (m, 5H), 2.76-2.83 (m, 1H), 2.91-2.96 (m, 1H), 3.23-3.31 (m, 1H), 4.04 (d, J=12.58 Hz, 1H), 4.40 (dd, J=10.13, 4.91 Hz, 1H), 7.50-7.58 (m, 3H), 7.70 (dd, J=10.59, 2.61 Hz, 1H), 8.45 (t, J=8.13 Hz, 1H).

Example 72

6-fluoro-2-(2-fluoro-4-(1-methylpiperidin-2-yl)phenyl)-1H-benzimidazole-4-carboxamide This compound was prepared according to the procedure for EXAMPLE 50 and substituting EXAMPLE 61 for EXAMPLE 50F and formaldehyde for acetaldehyde. $^1$H NMR (CD$_3$OD) δ 1.73-1.82 (m, 1H), 1.93-2.20 (m, 5H), 2.68 (s, 3H), 3.21-3.29 (m, 1H), 3.72 (d, J=13.43 Hz, 1H), 4.29 (dd, J=11.75, 3.51 Hz, 1H), 7.52-7.57 (m, 3H), 7.72 (dd, J=10.53, 2.59 Hz, 1H), 8.48 (t, J=7.93 Hz, 1H).

Example 73

6-chloro-2-(2-fluoro-4-piperidin-3-ylphenyl)-1H-benzimidazole-4-carboxamide

This compound was prepared according to the procedure for EXAMPLE 59 and substituting EXAMPLE 44B for EXAMPLE 45D. $^1$H NMR (CD$_3$OD) δ 1.86-2.01 (m, 2H), 2.08-2.16 (m, 2H), 3.05-3.13 (m, 1H), 3.20-3.28 (m, 2H), 3.48 (d, J=12.51 Hz, 1H), 3.53 (d, J=7.93 Hz, 1H), 7.50-7.55 (m, 2H), 8.01 (d, J=1.83 Hz, 1H), 8.11 (d, J=1.83 Hz, 1H), 8.18 (t, J=7.93 Hz, 1H).

Example 74

6-chloro-2-(4-piperidin-4-ylphenyl)-1H-benzimidazole-4-carboxamide

Example 74A tert-butyl 4-(4-(2-amino-3-carbamoyl-5-chlorophenylcarbamoyl)phenyl)piperidine-1-carboxylate A solution of 2,3-diamino-5-chlorobenzamide (0.75 g), tert-butyl 4-(4-carboxyphenyl)-piperidine-1-carboxylate (0.17 g), 1-hydroxybenzotriazole (HOBT, 0.22 g), benzotriazol-1-yl-oxytripyrrolidinophosphonium hexafluorophosphate (PyBOP, 0.85 g) and diisopropylethylamine (DIPEA, 0.85 mL) in DMF (5 mL) was stirred for 18 hours and concentrated. The concentrate was flash chromatographed on silica gel with 10% methanol/dichloromethane.

Example 74B 6-chloro-2-(4-piperidin-4-ylphenyl)-1H-benzimidazole-4-carboxamide A solution of EXAMPLE 74A (60 mg) in acetic acid (5 mL) at reflux was stirred for 60 minutes and concentrated. The concentrate was purified by chromatography on silica gel with 10% methanol/dichloromethane. 1H NMR (DMSO-d$_6$) δ 9.24 (s, 1H), 8.22 (d, J=7.98 Hz, 2H), 7.96 (s, 1H), 7.75-7.84 (m, 2H), 7.46 (d, J=8.29 Hz, 2H), 3.41 (d, J=12.27 Hz, 2H), 2.99-3.08 (m, 2H), 2.96 (t, J=3.53 Hz, 1H), 2.01 (d, J=12.27 Hz, 2H), 1.79-1.90 (m, 2H).

Example 75

2-(2-fluoro-4-(1-methylpiperidin-4-yl)phenyl)-1H-benzimidazole-4-carboxamide

A solution of EXAMPLE 26 (40 mg) and 37 wt % formaldehyde in water (45 mL) in methanol (3 mL) at ambient temperature was stirred for 1 hour, treated with sodium cyanoborohydride (38 mg), stirred at 50° C. for 18 hours, cooled and concentrated. The concentrate purified by HPLC (Zorbax C-8, 0.1% TFA/CH$_3$CN/water). The TFA salt was converted to the HCl salt by dissolving in methanol and treating with HCl in diethyl ether. $^1$H NMR (CD$_3$OD) δ 2.01-2.15 (m, 2H), 2.17-2.27 (m, 2H), 2.95 (s, 3H), 3.08-3.16 (m, 1H), 3.17-3.26 (m, 2H), 3.67 (d, J=12.58 Hz, 2H), 7.43-7.51 (m, 2H), 7.64 (t, J=7.98 Hz, 1H), 7.98 (d, J=7.98 Hz, 1H), 8.07 (dd, J=7.52, 0.77 Hz, 1H), 8.19 (t, J=7.98 Hz, 1H).

Example 76

6-chloro-2-(4-piperidin-3-ylphenyl)-1H-benzimidazole-4-carboxamide

This compound was prepared by substituting tert-butyl 3-(4-carboxyphenyl)piperidine-1-carboxylate for tert-butyl 4-(4-carboxyphenyl)piperidine-1-carboxylate in EXAMPLE 74. $^1$H NMR (DMSO-D6) δ 9.22 (s, 1H), 8.23 (d, J=8.29 Hz, 2H), 7.95 (s, 1H), 7.76-7.80 (m, 2H), 7.53 (d, J=7.98 Hz, 2H), 3.36-3.41 (m, 1H), 2.99-3.10 (m, 3H), 2.92 (s, 1H), 1.91-1.97 (m, 2H), 1.75-1.85 (m, 3H).

Example 77

6-fluoro-2-(4-piperidin-3-ylphenyl)-1H-benzimidazole-4-carboxamide

This compound was prepared by substituting 2,3-diamino-5-fluorobenzamide for 2,3-diamino-5-chlorobenzamide in EXAMPLE 76. $^1$H NMR (DMSO-D6) δ 9.22 (s, 1H), 8.22 (d, J=8.29 Hz, 2H), 7.94 (s, 1H), 7.55-7.62 (m, 2H), 7.51 (d, J=8.29 Hz, 2H), 3.02-3.12 (m, 3H), 2.90 (s, 1H), 1.91-1.97 (m, 2H), 1.75-1.86 (m, 3H).

Example 78

2-(4-(1-ethylpiperidin-4-yl)-2-fluorophenyl)-1H-benzimidazole-4-carboxamide

This compound was prepared according to procedure for EXAMPLE 75 and substituting acetaldehyde for formaldehyde. $^1$H NMR (CD$_3$OD) δ 1.44 (t, J=7.52 Hz, 3H), 1.74-1.87 (m, 1H), 2.05-2.20 (m, 2H), 2.20-2.32 (m, 2H), 3.11-3.21 (m, 1H), 3.56-3.67 (m, 3H), 3.69-3.78 (m, 1H), 3.79-3.88 (m, 1H), 7.46-7.54 (m, 2H), 7.68 (t, J=7.98 Hz, 1H), 8.01 (d, J=7.98 Hz, 1H), 8.09 (dd, J=7.52, 0.77 Hz, 1H), 8.17 (t, J=7.82 Hz, 1H).

Example 79

2-(2-fluoro-4-(1-isopropylpiperidin-4-yl)phenyl)-1H-benzimidazole-4-carboxamide

This compound was prepared according to procedure for EXAMPLE 75 and substituting acetone for formaldehyde H NMR (CD$_3$OD) δ 1.44 (d, J=6.75 Hz, 6H), 2.13-2.29 (m, 4H), 3.10-3.20 (m, 1H), 3.21-3.29 (m, 2H), 3.54-3.68 (m, 3H), 7.49-7.56 (m, 2H), 7.69-7.76 (m, 1H), 8.04 (dd, J=8.29, 0.61 Hz, 1H), 8.11 (dd, J=7.67, 0.61 Hz, 1H), 8.12-8.17 (m, 1H).

Example 80

6-chloro-2-(4-(1-cyclopropylmethylpiperidin-3-yl)-2-fluorophenyl)-1H-benzimidazole-4-carboxamide This compound was prepared according to procedure for EXAMPLE 75 and substituting EXAMPLE 73 for EXAMPLE 26 and cyclopropylaldehyde for formaldehyde. $^1$H NMR (CD$_3$OD) δ 0.43-0.50 (m, 2H), 0.75-0.84 (m, 2H), 1.14-1.24 (m, 1H), 1.80-1.88 (m, 1H), 1.95-2.06 (m, 1H), 2.15 (t, J=16.78 Hz, 2H), 3.00-3.12 (m, 3H), 3.15-3.26 (m, 2H), 3.76 (d, J=7.63 Hz, 2H), 7.33 (d, J=9.76 Hz, 2H), 7.75 (d, J=1.83 Hz, 1H), 7.87 (d, J=1.83 Hz, 1H), 8.29 (t, J=7.93 Hz, 1H).

Example 81

6-Fluoro-2-(2-fluoro-4-piperidin-4-ylphenyl)-1H-benzimidazole-4-carboxamide

This compound was prepared according to procedure for EXAMPLE 60 and substituting EXAMPLE 45D for EXAMPLE 44B and 4-tributylstannylpyridine for 2-trimethylstannylpyridine. $^1$H NMR (CD$_3$OD) δ 1.90-2.00 (m, 2H), 2.15 (d, J=14.04 Hz, 2H), 3.00-3.07 (m, 1H), 3.14-3.21 (m, 2H), 3.55 (d, J=12.82 Hz, 2H), 7.25 (d, J=12.82 Hz, 1H), 7.29 (d, J=7.93 Hz, 1H), 7.48 (dd, J=8.24, 2.44 Hz, 1H), 7.67 (dd, J=10.68, 2.44 Hz, 1H), 8.23 (t, J=7.93 Hz, 1H).

Example 82

6-Chloro-2-(4-(1-methylpiperidin-4-yl)phenyl)-1H-benzimidazole-4-carboxamide

Example 82A 4-(1-methylpiperidin-4-yl)benzoic acid

A solution of 4-piperidin-4-ylbenzoic acid (0.5 g) and 36% formaldehyde in water (0.175 mL) in methanol (5 mL) was treated with sodium cyanoborohydride (0.13 g) and acetic acid (0.5 mL), stirred for 18 hours and concentrated. The concentrate was flash chromatographed on silica gel with 10% methanol/dichloromethane.

Example 82B 6-chloro-2-(4-(1-methylpiperidin-4-yl)phenyl)-1H-benzimidazole-4-carboxamide A mixture of EXAMPLE 82A (0.089 g) and thionyl chloride (1 mL) was stirred for 18 hours at ambient temperature and concentrated. The concentrate was substituted for tert-butyl 4-(4-carboxyphenyl)piperidine-1-carboxylate in EXAMPLE 74. $^1$H NMR (DMSO-d$_6$) δ 9.14 (s, 1H), 8.24 (d, J=8.29 Hz, 2H), 7.93 (s, 1H), 7.76-7.80 (m, 2H), 7.47 (d, J=8.29 Hz, 2H), 3.51 (d, J=11.97 Hz, 2H), 3.02-3.08 (m, 2H), 2.86-2.95 (m, 1H), 2.79 (d, J=4.91 Hz, 3H), 1.99-2.07 (m, 3H).

Example 83

6-fluoro-2-(4-(1-methylpiperidin-4-yl)phenyl)-1H-benzimidazole-4-carboxamide

This compound was prepared by substituting 2,3-diamino-5-fluorobenzamide for 2,3-diamino-5-chlorobenzamide in EXAMPLE 82. $^1$H NMR (DMSO-D6) δ 9.64 (d, J=8.40 Hz, 2H), 9.10 (dd, J=10.72, 2.61 Hz, 1H), 9.02 (dd, J=8.26, 2.46 Hz, 1H), 8.97 (d, J=8.11 Hz, 2H), 4.94-4.98 (m, 2H), 4.56-4.60 (m, 2H), 4.41-4.47 (m, 1H), 4.28 (s, 3H) 3.54-3.58 (m, 2H) 3.45-3.51 (m, 2H).

Example 84

6-fluoro-2-(4-piperidin-2-ylphenyl)-1H-benzimidazole-4-carboxamide

This compound was prepared by substituting tert-butyl 2-(4-carboxyphenyl)piperidine-1-carboxylate for tert-butyl 4-(4-carboxyphenyl)piperidine-1-carboxylate in EXAMPLE 77. $^1$H NMR (DMSO-D6) δ 9.21 (s, 1H), 8.32 (d, J=8.59 Hz, 2H), 7.94 (s, 1H), 7.76 (d, J=8.29 Hz, 2H), 7.58-7.64 (m, 2H), 4.33 (s, 1H), 3.38 (s, 2H), 3.07 (s, 1H), 1.98 (s, 1H), 1.88-1.95 (m, 2H), 1.83 (d, J=2.45 Hz, 2H), 1.68 (s, 1H).

Example 85

6-fluoro-4-(1-methylpiperidin-2-ylphenyl)-1H-benzimidazole-4-carboxamide

This compound was prepared from EXAMPLE 84 using the conditions described in EXAMPLE 82A. 1H NMR (DMSO-D6) δ 9.31 (d, J=2.44 Hz, 1H), 8.17 (d, J=7.93 Hz, 2H), 7.96 (d, J=2.75 Hz, 1H), 7.51-7.60 (m, 4H), 2.97 (s, 1H), 2.86 (s, 1H), 2.07 (s, 1H), 1.89-1.98 (m, 4H), 1.76 (s, 1H), 1.65 (s, 3H), 1.46 (s, 1H), 1.35 (s, 1H).

Example 86

(+)-(R)-2-(2-fluoro-4-piperidin-2-ylphenyl)-1H-benzimidazole-4-carboxamide

Example 86A benzyl (R)-3-(4-methoxycarbonyl-3-fluorophenyl)piperidine-1-carboxylate 1 g of racemic EXAMPLE 60A was resolved on HPLC (Chiralcel OJ, 85:7.5:7.5 hexane/EtOH/MeOH) to afford 448 mg of the title compound as the faster-eluting R-enantiomer (100% e.e.) and 460 mg of the S-enantiomer (98% e.e.) as the slower-eluting fraction. MS (DCI): m/z 372 (M+H)$^+$.

Example 86B benzyl (R)-2-(4-carboxy-3-fluorophenyl)piperidine-1-carboxylate This compound was prepared according to the procedure for EXAMPLE 60B, substituting EXAMPLE 86A for EXAMPLE 60A. MS (DCI): m/z 358 (M+H)$^+$.

Example 86C benzyl (R)-2-[4-(2-amino-3-carbamoylphenylcarbamoyl)-3-fluorophenyl]piperidine-1-carboxylate A solution of EXAMPLE 86B (440 mg, 1.23 mmol) in a mixture of pyridine (5 mL) and DMF (5 mL) was treated with CDI (240 mg, 1.48 mmol) at 40° C. for 30 minutes. 2,3-Diaminobenzamide dihydrochloride (275 mg, 1.23 mmol) was added and the mixture was stirred at ambient temperature overnight. After concentration, the residue was partitioned between ethyl acetate and dilute aqueous sodium bicarbonate solution. The light yellow solid was collected by filtration, washed with water and ethyl acetate, and dried to give the title compound, which was used without further purification. MS (DCI/NH$_3$) m/z 491 (M+H)$^+$.

Example 86D benzyl-(R)-2-[4-carbamoyl-1H-benzimidazol-2-yl)-3-fluorophenyl]piperidine-1-carboxylate A suspension of EXAMPLE 86C in acetic acid (15 mL) was heated under reflux for 2 hours. After cooling, the solution was concentrated and the residue partitioned between ethyl acetate and aqueous sodium bicarbonate solution. The organic phase was washed with water, concentrated and purified by flash column chromatography (EtOAc) to provide 300 mg of title compound. MS (DCI/NH$_3$) m/z 473 (M+H)$^+$.

Example 86E (+)-(R)-2-(2-fluoro-4-piperidin-2-ylphenyl)-1H-benzimidazole-4-carboxamide The title compound was prepared according to the procedure for EXAMPLE 26, substituting EXAMPLE 86D for EXAMPLE 26B. $[\alpha]^{589}$+3.0. $^1$H NMR (CD$_3$OD) δ 1.77-1.97 (m, 2H); 1.97-2.13 (m, 3H); 2.16-2.24 (m, 1H); 3.20-3.30 (m, 1H); 3.56 (d, J=12.89 Hz, 1H); 4.49 (d, J=11.66 Hz, 1H); 7.66-7.73 (m, 3H); 8.02 (d, J=8.29 Hz, 1H); 8.11 (d, J=7.67 Hz, 1H); 8.30 (t, J=7.82 Hz, 1H).

Example 87

(−)-(S)-2-(2-fluoro-4-piperidin-2-ylphenyl)-1H-benzimidazole-4-carboxamide

The title compound was prepared according to the procedure for EXAMPLE 86, using the slower-eluting S-enantiomer of EXAMPLE 86A in place of the faster-eluting R-enantiomer. $[\alpha]^{589}$=−3.03. $^1$H NMR (CD$_3$OD); δ 1.78-1.88 (m, 1H); 1.90-2.13 (m, 3H); 2.19 (d, J=11.29 Hz, 1H); 3.22-3.33 (m, 2H); 3.57 (d, J=12.82 Hz, 1H); 4.48-4.56 (m, 1H); 7.72-7.82 (m, 3H); 8.07 (d, J=8.24 Hz, 1H); 8.13 (d, J=7.63 Hz, 1H); 8.25 (t, J=7.63 Hz, 1H). EXAMPLE 87 was synthesized as described below: EXAMPLE 87

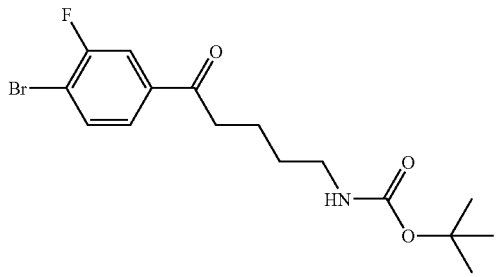 [SMILES: CC(C)(C)OC(=O)NCCCCC(=O)c1ccc(Br)c(F)c1]

tert-butyl 5-(4-bromo-3-fluorophenyl)-5-oxopentylcarbamate

To a solution of 1-bromo-2-fluoro-4-iodobenzene (44.22 g, 0.147 mol) in tetrahydrofuran (160 mL) was added isopropylmagnesium chloride (2.0 M solution in tetrahydrofuran, 73.5 mL) at 0° C. and the mixture stirred at 0° C. for 3 hours. This solution was cannulated into a solution of 1-BOC-2-piperidone (24.4 g, 0.122 mol) in tetrahydrofuran (240 mL) at −78° C. and the mixture stirred at −78° C. for 1 hour. The solution was warmed to ambient temperature and stirred for one hour before quenching with water. Hydrochloric acid (2N, 120 mL) was added and the mixture stirred at ambient temperature for 10 minutes. The mixture was concentrated and the residue partitioned between ethyl acetate and brine. The organic layer was washed with brine, dried over magnesium sulfate and filtered. Concentration afforded the crude product which was recrystallized from hexane and dichloromethane to give 33.95 g of the title compound as a white solid. $^1$HNMR (CDCl$_3$) δ 1.44 (s, 9H), 1.52-1.63 (m, 2H), 1.70-1.83 (m, 2H), 2.96 (t, J=7.1 Hz, 2H), 3.16 (q, J=6.4 Hz, 2H), 4.58 (s, 1H), 7.59-7.71 (m, 3H).

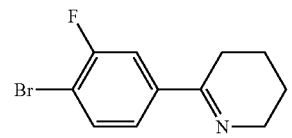 [SMILES: Fc1cc(C2=NCCCC2)ccc1Br]

Example 87B 6-(4-bromo-3-fluorophenyl)-2,3,4,5-tetrahydropyridine

A solution of EXAMPLE 87A (15.97 g, 42.67 mmol) in formic acid (200 mL) was heated at 40° C. for 5 hours. The reaction mixture was cooled, concentrated and the residue partitioned between ethyl acetate and dilute aqueous sodium hydroxide. The organic phase was washed with water, dried over magnesium sulfate, filtered and concentrated. The residue was purified by flash chromatography on silica gel, using a gradient of 20-60% ethyl acetate in hexane to give the title compound (9.5 g): MS (DCI): m/z 256, 258) (M+H)$^+$.

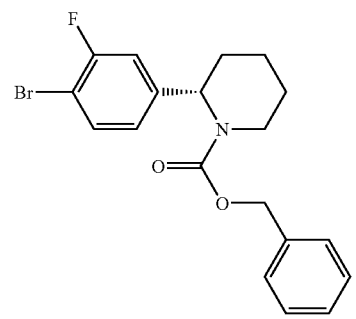 [SMILES: O=C(OCc1ccccc1)N1CCCC[C@H]1c1ccc(Br)c(F)c1]

Example 87C (S)-benzyl 2-(4-bromo-3-fluorophenyl)piperidine-1-carboxylate

EXAMPLE 87B (1.128 g, 4.4 mmol), bis(1,5-cyclooctadiene)diiridium dichloride (28.9 mg, 0.043 mmol), (R) (+)-2,2-bis(di-p-tolylphosphino)-1,1-binaphthyl (60 mg, 0.0884 mmol), methanol (5 mL) and benzylamine (47.1 µL, 0.431 mmol) were combined in a scintillation vial in a dry, inverted stirred reactor. This reactor was stirred magnetically for 45 minutes at ambient temperature under argon and was then pressurized with hydrogen. The mixture was stirred under hydrogen (900 psi) at ambient temperature for 3 days. Insoluble material was filtered off and filtrate concentrated. The residual oil was dissolved in a mixture of dioxane and water and treated with potassium carbonate (1.21 g) and benzyl chloroformate (743 μL) at ambient temperature overnight. The mixture was partitioned between ethyl acetate and brine. The organic phase was concentrated and the residue was purified by flash chromatography on silica gel using a gradient of 5-20% ethyl acetate in hexane to give the title compound (1.47 g).

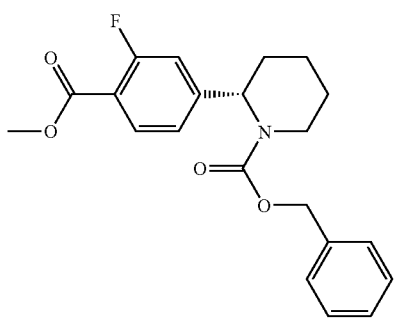 [SMILES: COC(=O)c1ccc([C@@H]2CCCCN2C(=O)OCc2ccccc2)cc1F]

Example 87D (S)-benzyl 2-(3-fluoro-4-(methoxycarbonyl)phenyl)piperidine-1-carboxylate A mixture of EXAMPLE 87C (1.46 g, 3.7 mmol), 1,1'-bis(diphenylphosphino)ferrocene palladium (II) dichloride (145 mg) and triethylamine (0.52 mL, 3.7 mmol) in methanol (16 mL) was stirred under 60 psi of carbon monoxide at 100° C. for 1 hour. After cooling to ambient temperature, the mixture was concentrated and the residue purified by flash chromatography on silica gel using a gradient of 10-40% ethyl acetate in hexane to give the title compound as a colorless oil (1.215 g). $[\alpha]^{589}=-102.2$ (c=0.95 in methanol).

Example 87E (−)-(S)-2-(2-fluoro-4-piperidin-2-ylphenyl)-1H-benzimidazole-4-carboxamide The title compound was prepared according to the procedure for EXAMPLE 86, using EXAMPLE 87D in place of EXAMPLE 86A.

Example 88

6-fluoro-2-(4-piperidin-4-ylphenyl)-1H-benzimidazole-4-carboxamide

Example 88A tert butyl 4-(4-(methoxy(methyl)carbamoyl)phenyl)piperidine-1-carboxylate A mixture of 4-(1-(tert-butoxycarbonyl)piperidin-4-yl)benzoic acid (0.7 g, 2.3 mmol), N,O-dimethylhydroxylamine (0.27 g, 2.8 mmol), 1-hydroxybenzotriazole (0.37 g, 2.7 mmol) and 1-ethyl-3-[3-dimethylaminopropyl]carbodiimide hydrochloride (1.1 g, 5.8 mmol) in tetrahydrofuran (15 mL) was stirred at ambient temperature for 48 hours. Additional N,O-dimethylhydroxylamine (0.14 g, 1 mmol) was added and the mixture stirred an additional 4 hours and concentrated. The residue was dissolved in ethyl acetate, washed with water and filtered through silica gel. The solution was concentrated and used without further purification.

Example 88B tert butyl 4-(4-formylphenyl)piperidine-1-carboxylate

A solution of EXAMPLE 88A (0.8 g, 2.3 mmol) in tetrahydrofuran (5 mL) was cooled to −78° C. and treated with lithium aluminum hydride (0.25 g, 6.6 mmol). The mixture was stirred for 30 minutes and treated with water (1 mL) and 15% sodium hydroxide (0.25 mL). Dichloromethane was added and the mixture dried over magnesium sulfate and filtered through silica gel. The solution was concentrated and purified by flash chromatography on silica gel using 1:1 hexane/ethyl acetate to provide the title compound (0.18 g).

Example 88C tert butyl 4-(4-(4-carbamoyl-6-fluoro-1H-benzimidazol-2-yl)phenyl)piperidine-1-carboxylate To a solution of EXAMPLE 45D (0.1 g, 0.6 mmol) and EXAMPLE 88B (0.18 g, 0.6 mmol) in methanol (10 mL) was added 10% palladium on carbon (0.06 g) and the mixture refluxed overnight. The mixture was cooled, filtered through a pad of celite, concentrated and used without further purification.

Example 88D 6-fluoro-2-(4-piperidin-4-ylphenyl)-1H-benzimidazole-4-carboxamide

A mixture of EXAMPLE 88C (0.26 g, 0.6 mmol) in dichloromethane (5 mL) was treated with trifluoroacetic acid (5 mL) and the mixture stirred at ambient temperature for 4 hours. The mixture was concentrated and purified by flash chromatography on silica gel using 0-10% methanol/dichloromethane/0.1% ammonium hydroxide, followed by HPLC on a C18 column using 0-100% acetonitrile/water/0.1% trifluoroacetic acid, to provide the title compound (0.131 g) as the trifluoroacetate salt. $^1$HNMR (DMSO-D6) δ 9.22 (s, 1H), 8.63 (s, 1H), 8.38 (s, 1H), 8.21 (d, J=8.3 Hz, 2H), 7.94 (s, 1H), 7.55-7.62 (m, 2H), 7.45 (t, J=7.7 Hz, 2H), 3.40 (s, 2H), 2.99-3.07 (m, 2H), 1.99 (s, 2H), 1.78-1.90 (m, 2H).

Example 89

(S)-2-(4-piperidin-2-ylphenyl)-1H-benzimidazole-4-carboxamide

The title compound was isolated as a side product in the synthesis of EXAMPLE 87. HNMR (CD$_3$OD) δ 1.77-1.88 (m, 2H), 1.94-2.19 (m, 4H), 3.21-3.27 (m, 1H), 3.53 (br d, J=12.8 Hz, 1H), 4.37 (dd, J=11.9, 2.7 Hz, 1H), 7.46 (t, J=7.9

Hz, 1H), 7.71 (d, J=8.5 Hz, 2H), 7.82 (d, J=7.3 Hz, 1H), 7.98 (d, J=6.7 Hz, 1H), 8.28 (d, J=8.2 Hz, 2H).

Example 90

(R)-2-(4-piperidin-2-ylphenyl)-1H-benzimidazole-4-carboxamide

The title compound was isolated as a side product in the synthesis of EXAMPLE 86. ¹HNMR (CD₃OD) δ 1.75-1.87 (m, 2H), 1.95-2.19 (m, 4H), 3.20-3.26 (m, 1H), 3.50-3.54 (m, 1H), 4.35-4.39 (m, 1H), 7.47 (t, J=7.9 Hz, 1H), 7.70 (d, J=8.3 Hz, 2H), 7.81 (d, J=7.1 Hz, 1H), 7.98 (d, J=7.7 Hz, 1H), 8.28 (d, J=8.2 Hz, 2H).

Example 91

6-fluoro-2-(4-(1-methylpiperidin-3-yl)phenyl)-1H-benzimidazole-4-carboxamide

Example 91A 4-(1-(methylpiperidin-3-yl)benzoic acid

A mixture of 4-piperidin-3-ylbenzoic acid trifluoroacetate (0.32 g, 1.1 mmol), sodium cyanoborohydride (0.066 g, 1.1 mmol), 36% aqueous formaldehyde (0.15 mL, 1.8 mmol) and acetic acid (0.5 mL) in methanol (4 mL) was stirred overnight at ambient temperature. The mixture was filtered through silica gel, concentrated and used without further purification.

Example 91B

N-methoxy-N-methyl-4-(1-methylpiperidin-3-yl) benzamide

The title compound was prepared as described in EXAMPLE 88A by substituting Example 91A for 4-(1-(tert-butoxycarbonyl)piperidin-4-yl)benzoic acid.

Example 91C 4-(1-methylpiperidin-3-yl)benzaldehyde

The title compound was prepared as described in EXAMPLE 88B by substituting EXAMPLE 91B for EXAMPLE 88A.

Example 91D 6-fluoro-2-(4-(1-methylpiperidin-3-yl)phenyl)-1H-benzimidazole-4-carboxamide The title compound was prepared as described in Example 88C by substituting EXAMPLE 91C for EXAMPLE 88B. The crude product was purified by flash chromatography on silica gel with 0-10% methanol/dichloromethane/0.1% ammonium hydroxide to provide the title compound. 1HNMR (DMSO-D6) δ 9.31 (s, 1H), 8.16 (d, J=8.2 Hz, 2H), 7.95 (s, 1H), 7.59 (dd, J=10.7, 2.4 Hz, 1H), 7.56 (dd, J=8.4, 2.3 Hz, 1H), 7.48 (d, J=8.2 Hz, 2H), 2.82-2.91 (m, 2H), 2.24 (s, 3H), 2.05 (t, J=10.1 Hz, 1H), 1.98 (t, J=10.7 Hz, 1H), 1.80-1.88 (m, 1H), 1.73 (td, J=6.4, 3.0 Hz, 1H), 1.64 (qt, J=12.5, 3.7 Hz, 1H) 1.45 (qd, J=12.2, 4.0 Hz, 1H).

Example 92

(+) (R)-2-(2-fluoro-4-pyrrolidin-2-ylphenyl)-1H-benzimidazole-4-carboxamide

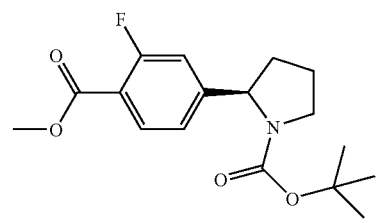 [SMILES: COC(=O)c1ccc([C@H]2CCCN2C(=O)OC(C)(C)C)cc1F]

Example 92A (R)-tert-butyl 2-(3-fluoro-4-(methoxycarbonyl)phenyl)pyrrolidine-1-carboxylate To a solution of N-BOC-pyrrolidine (3.0 mL, 17.1 mmol) and (−)-sparteine (3.9 mL, 17.1 mmol) in tert-butyl methyl ether (36 mL) at −78° C. was added sec-butyl lithium (1.4 M solution in cyclohexane, 12.21 mL, 17.1 mmol) and the mixture stirred at <−70° C. for 3 hours. A solution of zinc (II) chloride (1M solution in diethyl ether, 10.2 mL, 10.2 mmol) was added, the mixture stirred at −78° C. for 30 minutes and then warmed to ambient temperature. The mixture was stirred for 30 minutes and EXAMPLE 50A (3.32 g, 14.25 mmol), t-butylphosphine-tetrafluoroboric acid (249 mg, 0.855 mmol) and palladium (II) acetate (153 mg, 0.69 mmol) were added and the mixture stirred at ambient temperature overnight. Concentrated ammonium hydroxide (1 mL) was added and the mixture stirred at ambient temperature for 30 minutes. Insoluble material was filtered through Celite and washed with ethyl acetate. The filtrate was washed with 0.5 M hydrochloric acid and water and concentrated. The residue was purified by flash chromatography on silica gel, using a gradient of 10-30% ethyl acetate in hexane to give the title compound (2.66 g).

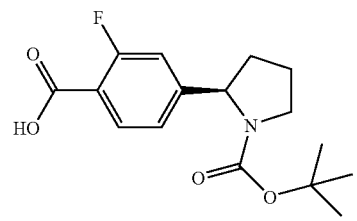 [SMILES: CC(C)(C)OC(=O)N1CCC[C@@H]1c1ccc(C(=O)O)c(F)c1]

Example 92B (R)-4-(1-(tert-butoxycarbonyl)pyrrolidin-2-yl)-2-fluorobenzoic acid To a solution of EXAMPLE 92A (2.65 g, 8.2 mmol) in tetrahydrofuran (20 mL) was added lithium hydroxide monohydrate (688 mg, 16.4 mmol) in 20 mL of water and methanol added until a transparent solution formed. This mixture was stirred at ambient temperature for 2 hours and acidified with 2N hydrochloric acid to pH 2. The mixture was concentrated to about 10 mL, diluted with water and let stand at ambient temperature overnight. The white solid was collected by filtration, washed with water and dried to give the title compound (2.21 g). Recrystallization from methanol and water gave 1.61 g of title compound.

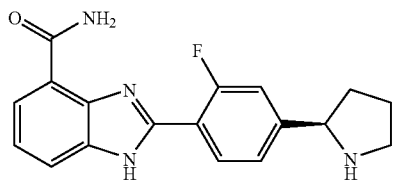 [SMILES: NC(=O)c1cccc2[nH]c(-c3ccc([C@H]4CCCN4)cc3F)nc12]

Example 92C (R)-2-(2-fluoro-4-(pyrrolidin-2-yl)phenyl)-1H-benzo[d]imidazole-4-carboxamide The title compound was prepared according to the procedure for EXAMPLES 50E and 50F, substituting EXAMPLE 92B for EXAMPLE 50D. The trifluoroacetate salt was dissolved in methanol and dichloromethane and 1M hydrochloric acid in diethyl ether added. Concentration afforded the title compound as the hydrochloride salt. $[\alpha]^{589}$=+7.3 (c=0.6 in methanol); $^1$H NMR (CD$_3$OD) δ 2.21-2.38 (m, 3H), 2.60-2.66 (m, 1H), 3.50-3.61 (m, 2H), 4.81-4.85 (m, 1H), 7.71-7.76 (m, 3H), 8.05 (d, J=8.2 Hz, 1H), 8.12 (d, J=7.6 Hz, 1H), 8.26 (t, J=7.8 Hz, 1H).

Example 93

(−) (S)-2-(2-fluoro-4-pyrrolidin-2-ylphenyl)-1H-benzimidazole-4-carboxamide

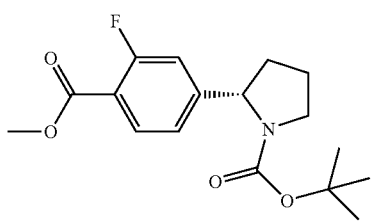 [SMILES: COC(=O)c1ccc([C@@H]2CCCN2C(=O)OC(C)(C)C)cc1F]

Example 93A (S)-tert-butyl 2-(3-fluoro-4-(methoxycarbonyl)phenyl)pyrrolidine-1-carboxylate Racemic EXAMPLE 50C (6.3 g) was resolved by chiral HPLC (Whelk 0, 95:2.5:2.5 hexane/ethanol/methanol) to give the title compound as the faster-diluting fraction (2.6 g, 100% e.e.), $[\alpha]^{589}$=−110.0 (c=0.65 in methanol) and EXAMPLE 92A as the slower-diluting fraction (2.7 g, 97.5 e.e.).

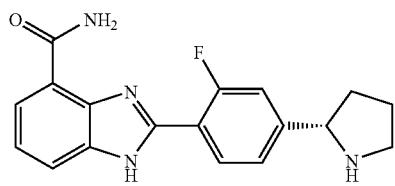 [SMILES: NC(=O)c1cccc2[nH]c(-c3ccc([C@@H]4CCCN4)cc3F)nc12]

Example 93B (−) (S)-2-(2-fluoro-4-pyrrolidin-2-ylphenyl)-1H-benzimidazole-4-carboxamide The title compound was prepared according to the procedure for EXAMPLE 92, substituting EXAMPLE 93A for EXAMPLE 92A. $[\alpha]^{589}$=−6.8 (c=0.7 in methanol); H NMR (CD$_3$OD) δ 2.22-2.37 (m, 3H), 2.60-2.65 (m, 1H), 3.50-3.61 (m, 2H), 4.81-4.86 (m, 1H), 7.71-7.77 (m, 3H), 8.05 (d, J=7.6 Hz, 1H), 8.12 (d, J=7.6 Hz, 1H), 8.26 (t, J=7.8 Hz, 1H).

The foregoing examples are meant to illustrate the invention but not to limit it. Variations and changes obvious to one skilled in the art are intended to be within the scope of the invention as defined in the claims.

What is claimed is:
1. A compound having formula (I)

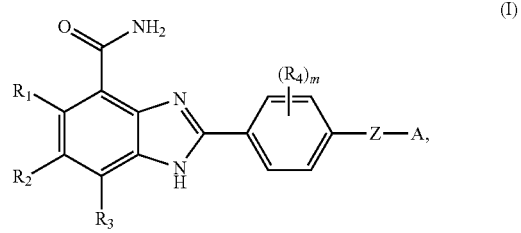

or a salt thereof, wherein
R$_1$, R$_2$, and R$_3$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, NR$_A$R$_B$, and (NR$_A$R$_B$)carbonyl;
each R$_4$ is independently selected from the group consisting of hydrogen, halogen, alkyl, and haloalkyl;
m is 4;
Z is a bond;
A is

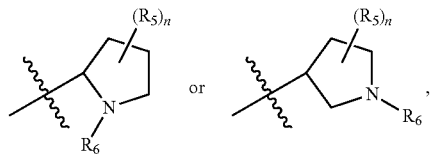

each R$_5$ is independently selected from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, heterocycle, heterocyclealkyl, heteroaryl, heteroarylalkyl, hydroxy, hydroxyalkyl, NR$_C$R$_D$, (NR$_C$R$_D$)alkyl, (NR$_C$R$_D$)carbonyl, (NR$_C$R$_D$)carbonylalkyl, and (NR$_C$R$_D$)sulfonyl;

R$_6$ is selected from the group consisting of hydrogen, alkenyl, alkoxyalkyl, alkoxycarbonyl, alkoxycarbonylalkyl, alkyl, alkynyl, aryl, arylalkyl, cycloalkyl, cycloalkylalkyl, heterocycle, heterocyclealkyl, heteroaryl, heteroarylalkyl, hydroxyalkyl, (NR$_C$R$_D$)alkyl, (NR$_C$R$_D$)carbonyl, (NR$_C$R$_D$)carbonylalkyl, and (NR$_C$R$_D$)sulfonyl;

n is 0, 1, 2, or 3; and

R$_A$, R$_B$, R$_C$, and R$_D$ are independently selected from the group consisting of hydrogen, alkyl, alkycarbonyl, and cycloalkyl.

2. The compound according to claim 1 having formula (I)

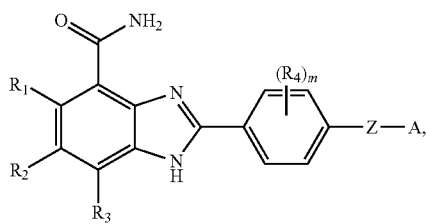

(I)

or a salt thereof, wherein

R$_1$, R$_2$, and R$_3$ are independently selected from the group consisting of hydrogen and halogen;

each R$_4$ is independently selected from the group consisting of hydrogen, halogen, and haloalkyl;

m is 4;

Z is a bond; and

R$^6$ is selected from the group consisting of alkoxycarbonyl, alkyl, arylalkyl, cycloalkyl, cycloalkylalkyl, and heterocyclealkyl.

3. The compound according to claim 1 wherein R$^4$ is hydrogen and R$^6$ is hydrogen.

4. The compound according to claim 1 wherein R$_1$, R$_2$, and R$_3$ are hydrogen.

5. The compound according to claim 1 wherein R$_2$ is halogen.

6. The compound according to claim 1 wherein each R$_4$ is hydrogen.

7. A compound selected from the group consisting of

21tert-butyl 2-(4-(4-carbamoyl-1H-benzimidazol-2-yl)phenyl)pyrrolidine-1-carboxylate;

232-(4-(1-isopropylpyrrolidin-3-yl)phenyl)-1H-benzimidazole-4-carboxamide;

242-(4-(1-cyclopentylpyrrolidin-3-yl)phenyl)-1H-benzimidazole-4-carboxamide;

252-(4-(1-cyclohexylpyrrolidin-3-yl)phenyl)-1H-benzimidazole-4-carboxamide;

292-(4-(1-isopropylpyrrolidin-2-yl)phenyl)-1H-benzimidazole-4-carboxamide;

302-(4-(1-cyclopropylmethylpyrrolidin-3-yl)phenyl)-1H-benzimidazole-4-carboxamide;

312-(4-(1-cyclopentylpyrrolidin-2-yl)phenyl)-1H-benzimidazole-4-carboxamide;

322-(4-(1-cyclohexylpyrrolidin-2-yl)phenyl)-1H-benzimidazole-4-carboxamide;

332-(4-pyrrolidin-2-ylphenyl)-1H-benzimidazole-4-carboxamide;

342-(4-(1-propylpyrrolidin-3-yl)phenyl)-1H-benzimidazole-4-carboxamide;

352-(4-(1-cyclopropylmethylpyrrolidin-2-yl)phenyl)-1H-benzimidazole-4-carboxamide;

362-(4-(1-propylpyrrolidin-2-yl)phenyl)-1H-benzimidazole-4-carboxamide;

383-(4-pyrrolidin-2-ylphenyl)-1H-benzimidazole-4-carboxamide;

392-(4-(1-methylpyrrolidin-2-yl)phenyl)-1H-benzimidazole-4-carboxamide;

402-(4-(1-methylpyrrolidin-3-yl)phenyl)-1H-benzimidazole-4-carboxamide;

446-chloro-2-(4-pyrrolidin-2-ylphenyl)-1H-benzimidazole-4-carboxamide;

456-Fluoro-2-(4-pyrrolidin-2-ylphenyl)-1H-benzimidazole-4-carboxamide;

466-chloro-2-(4-(1-isopropyl-pyrrolidin-2-yl)phenyl)-1H-benzimidazole-4-carboxamide;

476-chloro-2-(4-(1-cyclopentyl-pyrrolidin-2-yl)phenyl)-1H-benzimidazole-4-carboxamide;

486-Chloro-2-(4-(1-methylpyrrolidin-2-yl)phenyl)-1H-benzimidazole-4-carboxamide;

496-fluoro-2-(4-(1-methylpyrrolidin-2-yl)phenyl)-1H-benzimidazole-4-carboxamide;

50F2-(2-fluoro-4-pyrrolidin-2-ylphenyl)-1H-benzimidazole-4-carboxamide;

502-(4-(1-ethylpyrrolidin-2-yl)-2-fluorophenyl)-1H-benzimidazole-4-carboxamide;

512-(2-fluoro-4-(1-isopropylpyrrolidin-2-yl)phenyl)-1H-benzimidazole-4-carboxamide;

522-(4-(1-Cyclobutylpyrrolidin-2-yl)-2-fluorophenyl)-1H-benzimidazole-4-carboxamide;

532-(2-Fluoro-4-(1-propylpyrrolidin-2-yl)phenyl)-1H-benzimidazole-4-carboxamide;

542-(4-(1-cyclopropylmethylpyrrolidin-2-yl)-2-fluorophenyl)-1H-benzimidazole-4-carboxamide;

556-fluoro-2-(2-fluoro-4-pyrrolidin-2-ylphenyl)-1H-benzimidazole-4-carboxamide;

566-fluoro-2-(2-fluoro-4-(1-isopropylpyrrolidin-2-yl)phenyl)-1H-benzimidazole-4-carboxamide;

572-(4-(1-Ethylpyrrolidin-2-yl)-2-fluorophenyl)-6-fluoro-1H-benzimidazole-4-carboxamide;

56-Fluoro-2-(2-fluoro-4-(1-methylpyrrolidin-2-yl)phenyl)-1H-benzimidazole-4-carboxamide;

92(+)(R)-2-(2-fluoro-4-pyrrolidin-2-ylphenyl)-1H-benzimidazole-4-carboxamide; and 93(−)(S)-2-(2-fluoro-4-pyrrolidin-2-ylphenyl)-1H-benzimidazole-4-carboxamide.

8. A composition comprising a compound having formula (I) of claim or salt thereof, and therapeutically acceptable carrier.

* * * * *